(12) United States Patent
Richardson et al.

(10) Patent No.: US 11,110,234 B2
(45) Date of Patent: *Sep. 7, 2021

(54) MEDICINAL INHALER REFILL ASSEMBLIES COMPRISING A LOCKOUT MECHANISM

(71) Applicant: KINDEVA DRUG DELIVERY L.P., St. Paul, MN (US)

(72) Inventors: William T. Richardson, Royston (GB); Robert May, Ely (GB); Christopher B. J. Groombridge, Stevenage (GB)

(73) Assignee: Kindeva Drug Delivery L.P., St. Paul, MN (US)

( * ) Notice: Subject to any disclaimer, the term of this patent is extended or adjusted under 35 U.S.C. 154(b) by 174 days.

This patent is subject to a terminal disclaimer.

(21) Appl. No.: 16/090,300

(22) PCT Filed: Apr. 4, 2017

(86) PCT No.: PCT/US2017/025883
§ 371 (c)(1),
(2) Date: Oct. 1, 2018

(87) PCT Pub. No.: WO2017/176704
PCT Pub. Date: Oct. 12, 2017

(65) Prior Publication Data
US 2019/0111221 A1 Apr. 18, 2019

Related U.S. Application Data

(60) Provisional application No. 62/318,557, filed on Apr. 5, 2016.

(51) Int. Cl.
*A61M 15/00* (2006.01)
*B65D 83/38* (2006.01)
(Continued)

(52) U.S. Cl.
CPC ........ *A61M 15/002* (2014.02); *A61M 15/009* (2013.01); *A61M 15/0081* (2014.02);
(Continued)

(58) Field of Classification Search
CPC ............ A61M 15/002; A61M 15/0001; A61M 15/0081; A61M 15/0091; A61M 15/0095;
(Continued)

(56) References Cited

U.S. PATENT DOCUMENTS

| 5,392,768 A | * | 2/1995 | Johansson ............. A61M 15/00 128/200.14 |
| 5,394,866 A | | 3/1995 | Ritson et al. |

(Continued)

FOREIGN PATENT DOCUMENTS

| EP | 0 689 848 | 1/1996 |
| GB | 2 263 068 | 7/1993 |

(Continued)

*Primary Examiner* — Valerie L Woodward
*Assistant Examiner* — Paige Kathleen Bugg
(74) *Attorney, Agent, or Firm* — Mueting Raasch Group

(57) ABSTRACT

A refill assembly (129) for use in a medicinal inhaler (100). The refill assembly includes a patient port (110), and an adapter (118) configured to cause a dose of medicament to be released. The adapter is movable between a first position in which a dose of medicament is not released and a second position in which a dose of medicament is released. The refill assembly further includes a lockout member (117) movable between (i) a first (locked) position in which the adapter is not movable from its first position to its second position, and (ii) a second (unlocked) position in which the adapter is movable from its first position to its second position.

20 Claims, 18 Drawing Sheets

(51) Int. Cl.
    *B65D 83/26*     (2006.01)
    *B65D 83/54*     (2006.01)

(52) U.S. Cl.
    CPC .... *A61M 15/0091* (2013.01); *A61M 15/0095* (2014.02); *B65D 83/265* (2013.01); *B65D 83/386* (2013.01); *A61M 15/0021* (2014.02); *A61M 15/0026* (2014.02); *A61M 2205/276* (2013.01); *A61M 2205/3569* (2013.01); *A61M 2205/50* (2013.01); *A61M 2205/502* (2013.01); *B65D 83/54* (2013.01)

(58) Field of Classification Search
    CPC ............ A61M 15/009; A61M 15/0021; A61M 15/0026; A61M 2205/276; A61M 2205/3569; A61M 2205/50; A61M 2205/502; B65D 83/265; B65D 83/386; B65D 83/54
    USPC .................................................. 123/200.23
    See application file for complete search history.

(56) References Cited

U.S. PATENT DOCUMENTS

| | | | |
|---|---|---|---|
| 6,637,432 | B2 | 10/2003 | Wakefield et al. |
| 7,219,664 | B2 | 5/2007 | Ruckdeschel et al. |
| 8,082,918 | B2 | 12/2011 | Jansen et al. |
| 8,141,550 | B2 * | 3/2012 | Lawrence ............... G09F 11/04 128/200.17 |
| 2008/0156321 | A1 * | 7/2008 | Bowman ........... A61M 15/0071 128/200.23 |
| 2008/0173301 | A1 * | 7/2008 | Deaton ............. A61M 15/0091 128/203.12 |
| 2009/0314372 | A1 * | 12/2009 | Ruskewicz ....... A61M 15/0086 138/46 |
| 2019/0111220 | A1 * | 4/2019 | Richardson ......... A61M 15/009 |
| 2020/0046916 | A1 * | 2/2020 | May .................... A61M 15/009 |

FOREIGN PATENT DOCUMENTS

| | | |
|---|---|---|
| GB | 2 266 466 | 11/1993 |
| GB | 2 360 218 | 9/2001 |
| GB | 2 385 845 | 3/2006 |
| WO | WO 1992/12799 | 8/1992 |
| WO | WO 2000/16837 | 3/2000 |
| WO | WO 2001/41849 | 6/2001 |
| WO | WO 2003/090824 | 11/2003 |
| WO | WO 2017/112476 | 6/2007 |
| WO | WO 2008/016698 | 2/2008 |
| WO | WO 2012/041938 | 4/2012 |
| WO | WO 2015/034709 | 3/2015 |
| WO | WO 2017/112400 | 6/2017 |
| WO | WO 2017/112451 | 6/2017 |
| WO | WO 2017/112452 | 6/2017 |
| WO | WO 2017/112748 | 6/2017 |
| WO | WO 2017/176693 | 10/2017 |

* cited by examiner

MEDICINAL INHALER REFILL ASSEMBLIES COMPRISING A LOCKOUT MECHANISM

CROSS REFERENCE TO RELATED APPLICATIONS

This application is a national stage filing under 35 U.S.C. 371 of PCT/US2017/025883, filed Apr. 4, 2017, which claims the benefit of U.S. Provisional Patent Application No. 62/318,557, filed Apr. 5, 2016, the disclosure of which is incorporated by reference in its/their entirety herein.

FIELD

The present disclosure generally relates to medicinal inhaler refill assemblies comprising a lockout mechanism, and medicinal inhalers comprising such a refill assembly and a reusable assembly.

BACKGROUND

Delivery of aerosolized medicament to the respiratory tract for the treatment of respiratory and other diseases is conventionally done using inhalers of either the pressurised metered dose inhaler (pMDI), the dry powder inhaler (DPI) or the nebulizer type. pMDI inhalers in particular have become an industry standard, and are familiar to many patients who suffer from either asthma or from chronic obstructive pulmonary disease (COPD). Conventional pMDI devices comprise an aluminum canister, sealed with a metering valve, which contains the medicament formulation. Generally, the medicament formulation is a pressurized formulation containing either fine particles of one or more medicinal compounds suspended in a liquefied hydrofluoroalkane (HFA) propellant, or a solution of one or more medicinal compounds dissolved in a propellant/co-solvent system. Formulations incorporating one drug in solution and another one in suspension form are also known.

In a conventional pulmonary pMDI, the sealed canister is provided to the patient in an actuator. The actuator is conventionally a generally L-shaped plastic molding comprising a generally cylindrical vertical tube that surrounds the canister plus a generally horizontal tube that forms a patient port (e.g., a mouthpiece or nosepiece) that defines an inspiration (or inhalation) orifice. To use such an inhaler, the patient exhales, places the patient port into a body cavity (e.g., a mouth or nose) and then inhales to draw air through the inspiration orifice. The majority of such inhalers are of the pulmonary "press-and-breathe" type, where the patient must press down on the protruding end of the canister in order to operate the metering valve to release a metered dose of medicament from the canister into the inhaled air stream and thence through the mouthpiece into their lungs. This requires a significant degree of coordination of timing of inhalation and dose release if the emerging cloud of aerosolized medicament is to be taken far enough into the lungs to provide maximum therapeutic benefit. If the patient releases the dose before inspiratory flow has been established, then a proportion of the drug is likely to be lost in the mouthpiece or the patient's mouth. Conversely, if released much after the start of inhalation, then the deeper regions of the lungs might already be full of air and not penetrated by the following bolus of released medicament aerosol.

Spacer devices have previously been devised which fit onto the mouthpiece of a pMDI in order to reduce the velocity of the emergent plume of medicament aerosol and to provide a volume in which it can expand and its propellant can evaporate more completely. This serves to avoid some of the problems of coordination and also avoids the tendency for high throat deposition caused by excessively fast drug particle inhalation. However, spacer devices are very bulky, and they can retain an excessive proportion of the drug on their walls, thereby reducing the dose that reaches the patient. Spacer devices can also be highly sensitive to electrostatic charge, which can often be strongly affected by the way in which they are washed or dried.

To overcome what can be quite a challenge for some patients, pMDI device designs have been created that employ automatic breath-actuated triggering, releasing a dose only in response to the patient's inhaled breath. The AUTOHALER™ metered dose inhaler, available from 3M Company, St. Paul, Minn., and the EASIBREATHE™ inhaler, available from Teva Pharmaceutical Industries Ltd., Israel, are two such pMDI devices that use breath-actuation to attempt to better coordinate dose release with inhalation.

SUMMARY

The present disclosure generally relates to medicinal inhaler refill assemblies comprising a lockout mechanism, such that the refill assemblies cannot be operated alone, but rather can be operated when coupled to a reusable assembly, e.g., to form an inhaler.

Some aspects of the present disclosure provide a refill assembly for use in a medicinal inhaler and configured to be removably coupled to a reusable assembly of a medicinal inhaler. The refill assembly can include a patient port, and an adapter configured to cause a dose of medicament to be released. The adapter can be movable between a first position in which a dose of medicament is not released and a second position in which a dose of medicament is released. The refill assembly can further include a lockout member movable between (i) a first position in which the adapter is not movable from its first position to its second position, and (ii) a second position in which the adapter is movable from its first position to its second position. The lockout member is in its first position when the refill assembly is not coupled to a reusable assembly and is in its second position when the refill assembly is coupled to a reusable assembly.

Other features and aspects of the present disclosure will become apparent by consideration of the detailed description and accompanying drawings.

DETAILED DESCRIPTION

Figure 1:
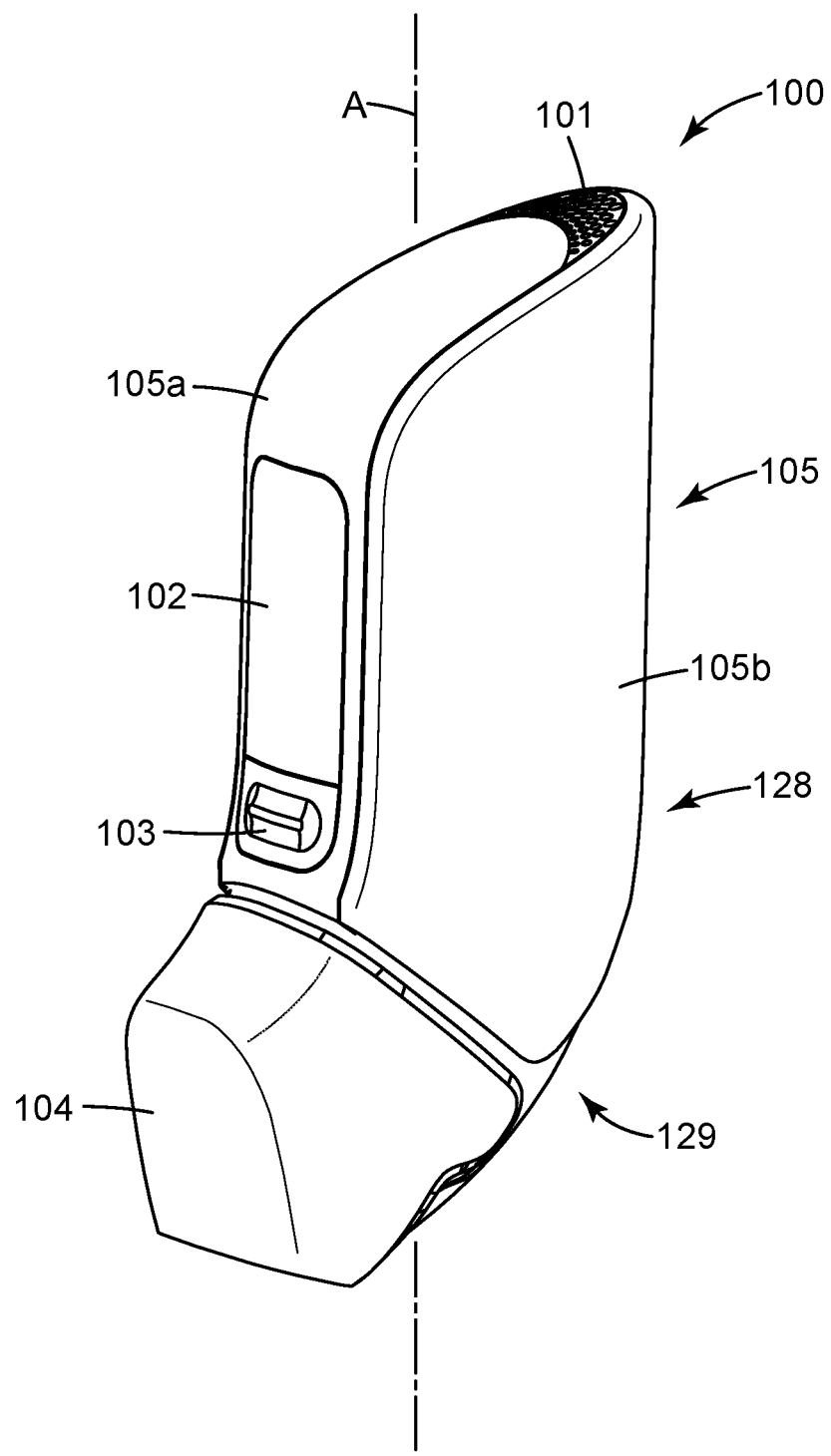
FIG. 1 is a front isometric view of a medicinal inhaler according to one embodiment of the present disclosure, the inhaler comprising a reusable assembly according to one embodiment of the present disclosure and a refill assembly according to one embodiment of the present disclosure, the inhaler shown assembled.

The present disclosure generally relates to medicinal inhaler refill assemblies comprising a lockout mechanism, such that the refill assemblies cannot be operated alone, but rather can be operated when coupled to a reusable assembly, e.g., to form an inhaler. Such a reusable assembly can include one or more of flow governing means, means for causing a dose to be fired from the inhaler, means for actuating a dose release firing system based on patient inhalation, and means for storing various data that can be viewed and/or retrieved, such as inhaler data (e.g., such as inhaler operation or inhaler function information), patient data (e.g., inhalation profiles, etc.), and the like.

Inhaler refill assemblies of the present disclosure are particularly suitable for use in an electronically triggered, breath-actuated pMDI but could also be incorporated into a dry powder inhaler or nebulizer. That is, refill assemblies of the present disclosure are suitable for use in a variety of inhalers, including but not limited to, one or more of a pressurized metered dose inhaler (pMDI) (e.g., a press-and-breathe pMDI, a mechanical (i.e., mechanically triggered) breath-actuated pMDI, an electronic (i.e., an electronically triggered) breath-actuated pMDI, or a combination thereof); a dry powder inhaler (e.g., a single dose (e.g., capsule) DPI, a multi-dose (e.g., tape based, or reservoir based) DPI, or a combination thereof); a nebulizer (e.g., a pocket nebulizer); or a combination thereof.

GB Patent No. 2266466 discloses an exemplary electronically triggered breath-actuated pMDI that could be modified to incorporate a refill assembly of the present disclosure. PCT Publication No. WO 2015/34709 discloses an exemplary DPI that could be modified to incorporate a refill assembly of the present disclosure. PCT Publication No. WO 92/12799 discloses an exemplary pocket nebulizer that could be modified to incorporate a refill assembly of the present disclosure. A refill assembly of the present disclosure can be used in any of the inhalers disclosed in GB Patent No. 2266466, PCT Publication No. WO 2015/34709, PCT Publication No. WO 92/12799 (each of which is incorporated herein by reference in its entirety), or a combination thereof.

Definitions

The terms "a", "an", and "the" are used interchangeably, with "at least one" meaning one or more of the elements being described.

The term "and/or" means either or both. For example "A and/or B" means only A, only B, or both A and B.

The terms "including," "comprising," or "having," and variations thereof, are meant to encompass the items listed thereafter and equivalents thereof as well as additional items.

Unless specified or limited otherwise, the terms "connected," "supported," and "coupled" and variations thereof are used broadly and encompass both direct and indirect connections, supports, and couplings. Further, "connected" and "coupled" are not restricted to physical or mechanical connections or couplings.

As used herein, the term "annular" or derivations thereof can refer to a structure having an outer edge and an inner edge, such that the inner edge defines an opening. For example, an annular structure can have a circular or round shape (e.g., a circular ring) or any other suitable shape, including, but not limited to, triangular, rectangular, square, trapezoidal, polygonal, etc., or combinations thereof. Furthermore, an annular structure of the present invention need not necessarily be symmetrical, but rather can be an asymmetrical or irregular shape; however, certain advantages may be possible with symmetrical and/or circular shapes.

The present disclosure generally relates to medicinal inhaler refill assemblies comprising a lockout mechanism, and inhalers comprising such refill assemblies. Refill assemblies of the present disclosure are particularly suitable for use in various types of inhalers for the delivery of doses of medicament in the form of aerosols to the respiratory tract, including oral pulmonary inhalers and nasal inhalers. In some embodiments, the refill assemblies of the present disclosure can be incorporated into breath-actuated inhalers that respond to a patient's inhalation. For example, in some embodiments, a refill assembly of the present disclosure can be configured to be incorporated in, or form a portion of, an electronically breath-actuated inhaler, a mechanically breath-actuated inhaler, or a combination thereof.

In some embodiments, refill assemblies of the present disclosure can include:
(a) a patient port;
(b) an adapter configured to cause a dose of medicament to be released, the adapter movable between a first position (e.g., a first axial position) in which a dose of medicament is not released and a second position (e.g., a second axial position) in which a dose of medicament is released; and
(c) a lockout member movable between:
   (i) a first position (e.g., relative to the adapter) in which the adapter is not movable (e.g., relative to the lockout member) from its first position to its second position, i.e., is locked, and
   (ii) a second position (e.g., relative to the adapter) in which the adapter is movable (e.g., relative to the lockout member) from its first position to its second position, i.e., is unlocked;
wherein the lockout member is in its first position when the refill assembly is not coupled to a reusable assembly and is in its second position when the refill assembly is coupled to a reusable assembly.

In some embodiments, the adapter can be configured to receive at least a portion of a canister (e.g., a pressurized metered dose inhaler (pMDI) canister), the canister comprising a medicament and a dose release valve, the adapter movable between a first position in which the dose release valve is not actuated to release a dose of medicament and a second position in which the dose release valve is actuated to release a dose of medicament.

In some embodiments, inhalers of the present disclosure can include a refill assembly of the present disclosure and can further include a reusable assembly of the present disclosure that is configured to be coupled to the refill assembly and includes a dose release firing system (e.g., a breath-actuated dose release firing system) configured to cause the adapter to move from its first position to its second position to release a dose of medicament. The lockout member, as described above, is in its first position (i.e., locking the adapter in its first position) when the refill assembly and the reusable assembly are decoupled. Movement of the lockout member from its first position to its second position can occur in response to coupling the refill assembly and the reusable assembly together. As a result, when the refill assembly is coupled to the reusable assembly: the lockout member is in its second position, the adapter is unlocked and free to move from its first position to its second position, and the dose release firing system of the reusable assembly is positioned relative to the adapter to be able to fire to cause the adapter to move to its second position.

Some embodiments of reusable assemblies of the present disclosure can include a firing system that provides a means of releasing stored energy (e.g., stored in a stored energy device, such as a biasing element, e.g., a spring), and in some cases, a significant amount of stored energy. In some embodiments, such a firing system can be used to operate a canister aerosol dose dispensing mechanism in response to detection of patient inhalation through a pMDI inhaler.

The present disclosure will be described with respect to particular embodiments and with reference to certain drawings, but the invention is not limited thereto. The drawings described are only schematic and are non-limiting. In the drawings, the size of some of the elements may for illustrative purposes be exaggerated and not drawn to scale. Where possible, analogous features in different embodiments have generally been denoted by similar numerals (e.g., 105, 1005, etc.).

FIGS. 1-6 illustrate a medicinal inhaler 100 according to one embodiment of the present disclosure. By way of example only, the inhaler 100 is a breath-actuated inhaler, and particularly, a breath-actuated pressurized metered dose inhaler (pMDI).

Figure 2:
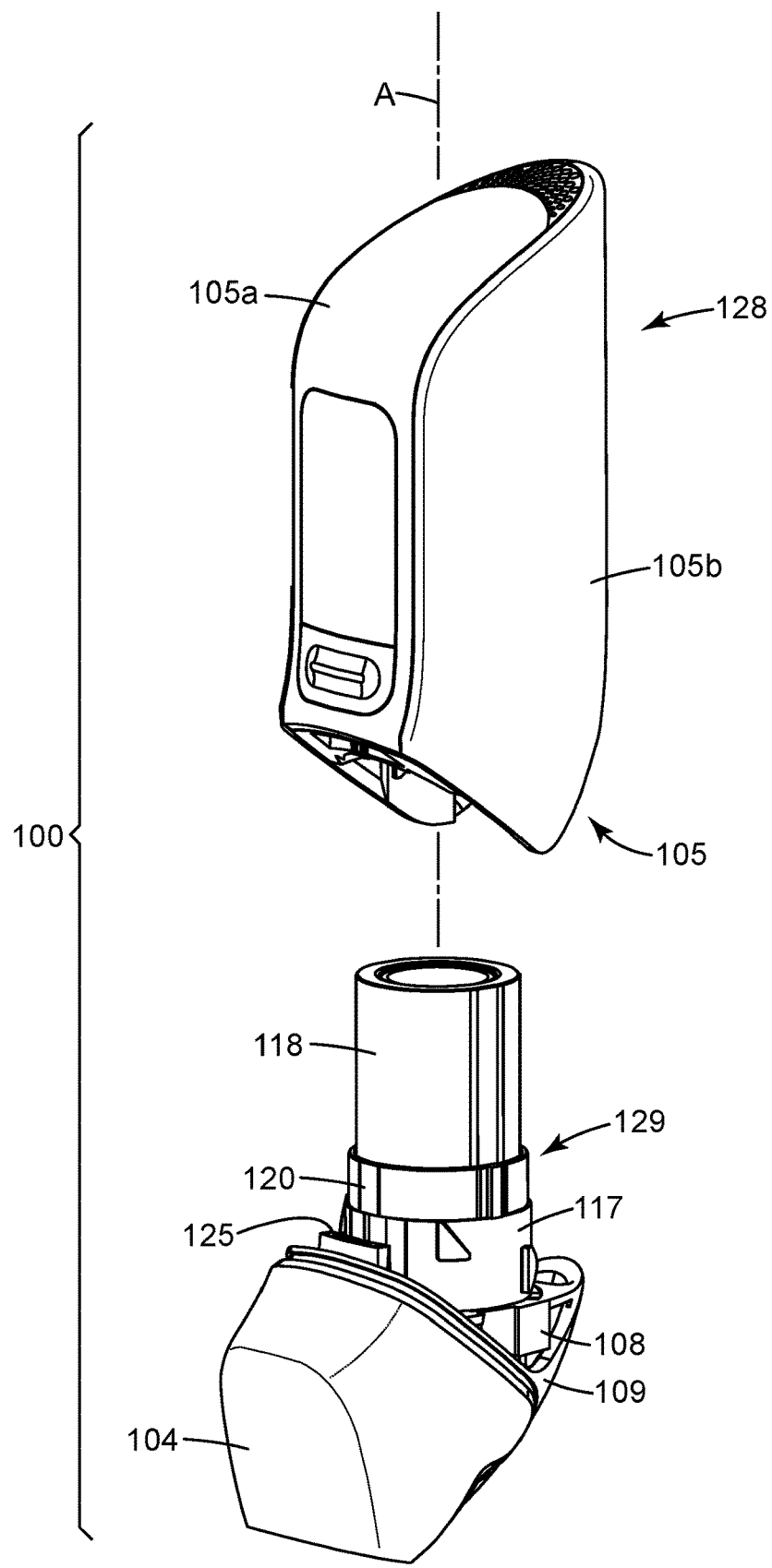
FIG. 2 is an exploded front isometric view of the inhaler of FIG. 1, the refill assembly shown separated from the reusable assembly; the reusable assembly including an outer housing having a first portion and a second portion, and an inner housing; the refill assembly including an adapter, a lower cam linkage, a lockout member, an air sealing cap, an actuator, and a patient port cover.

As shown in FIGS. 1 and 2, the inhaler 100 can include a reusable assembly 128 according to one embodiment of the present disclosure, and a refill assembly 129 according to one embodiment of the present disclosure. Particularly, the refill assembly 129 is locked when not coupled to a reusable assembly, such that a dose of medicament cannot be released from the refill assembly 129 until or unless the refill assembly 129 is coupled to a reusable assembly 128 (e.g., to form the inhaler 100).

As shown in FIGS. 1-4, the inhaler 100 (or a portion thereof, such as the reusable assembly 128 and/or the refill assembly 129) can include an axis (e.g., a longitudinal axis) A that defines an axial direction that extends along or substantially parallel to the axis A. In some embodiments, as shown, the refill assembly 129 and a reusable assembly 128 can be configured to be coupled together by moving the refill assembly 129 and the reusable assembly 128 toward one another in the axial direction (e.g., along the axis A).

As shown in FIGS. 1-2, the inhaler 100 can include an air inlet (or aspiration orifice) 101, a display including a display screen 1001 and a display cover 102, a control button 103, a patient port cover (e.g., a mouthpiece cover) 104, and an outer housing 105 comprising a first (e.g., front) portion 105a and a second (e.g., rear) portion 105b. The second portion 105b is sometimes referred to herein as a "slide cover." By way of example, the air inlet 101, the display cover 102, the control button 103, and the outer housing 105 are shown as forming a portion of the reusable assembly 128, and the patient port cover 104 (and underlying patient port) is shown as forming a portion of the refill assembly 129. In some embodiments, the air inlet 101 can include a grill, screen or grate positioned to inhibit debris from entering the air inlet 101.

Figure 3:
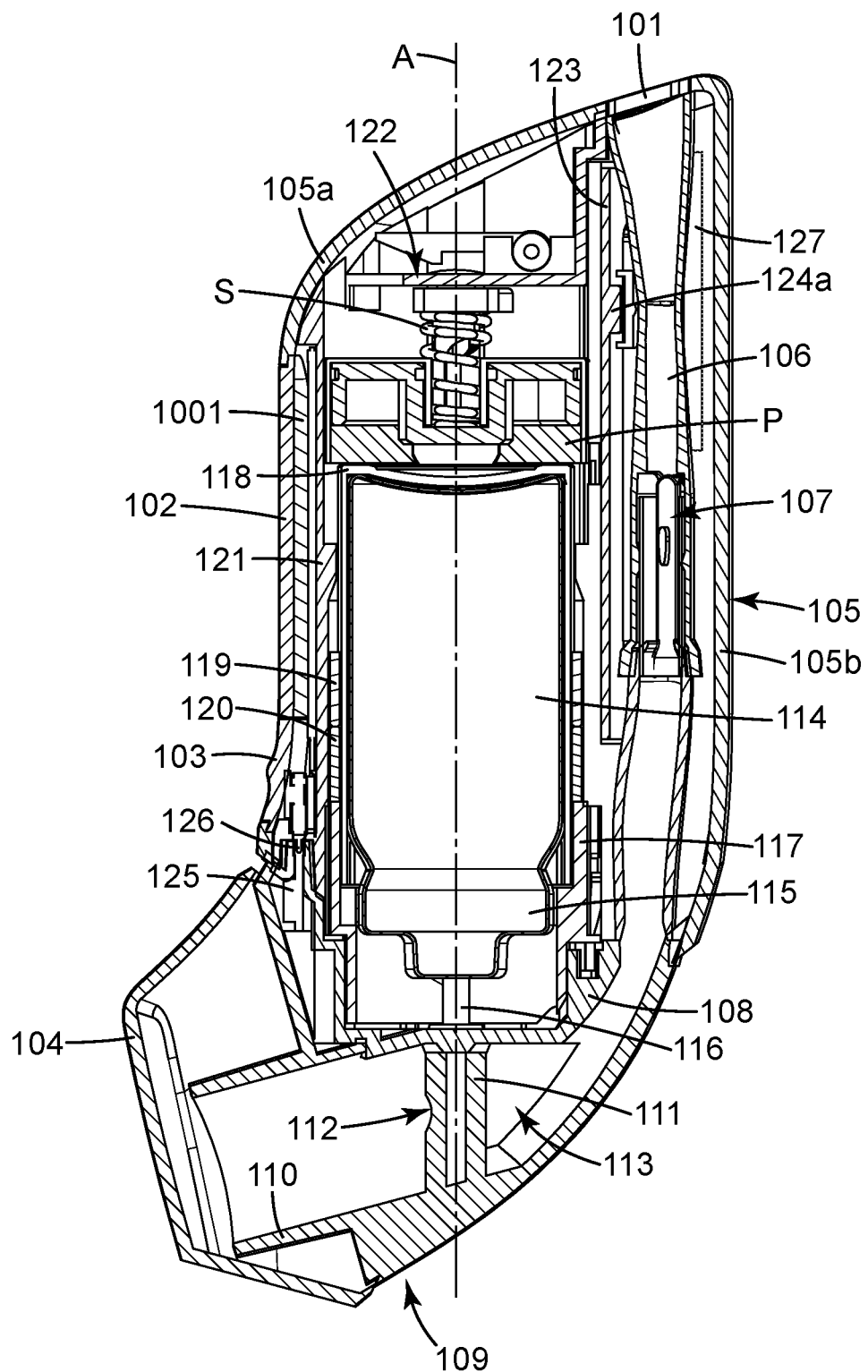
FIG. 3 is a side cross-sectional view of the inhaler of FIGS. 1 and 2, shown assembled.
Figure 4:
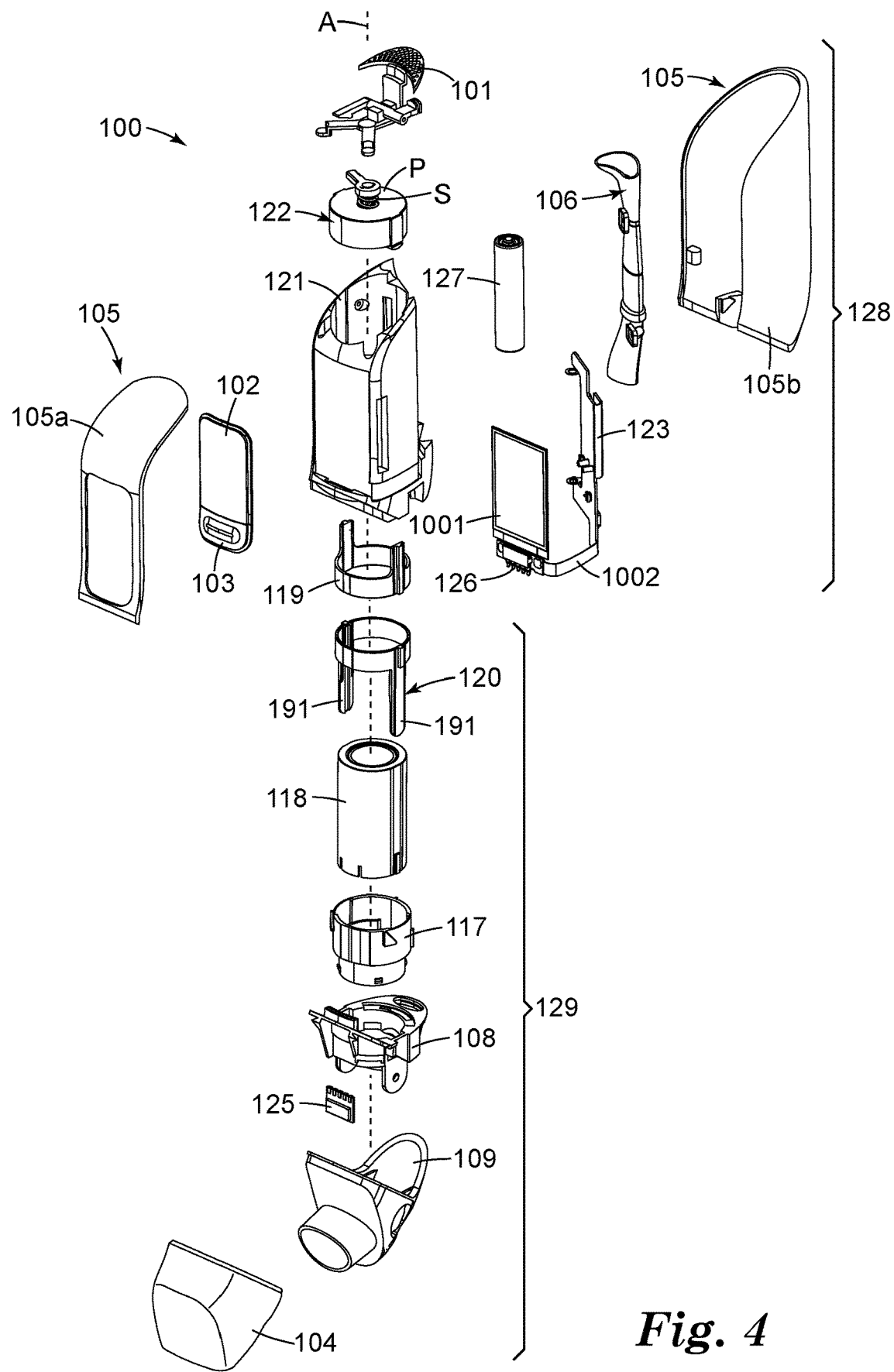
FIG. 4 is an exploded front isometric view of the inhaler of FIGS. 1-3, with the reusable assembly and the refill assembly each shown disassembled.

As shown in FIGS. 2-4, in some embodiments, the refill assembly 129 can include an adapter 118 (e.g., an adapter dimensioned to receive a medicament canister 114—see FIG. 3), a lower cam linkage 120, a lockout member 117, an air sealing cap 108, an actuator 109, a patient port cover 104, and a memory device 125. The memory device 125 can be configured to be operatively coupled to a controller 123 (described below), which can be located in a reusable assembly, i.e., when the refill assembly and the reusable assembly are coupled together. Various features of the refill assembly 129 and the reusable assembly 128 and how they interact or engage to prevent use of the refill assembly 129 when not coupled to the reusable assembly 128 are described in greater detail below.

By employing a refill assembly 129 that can be coupled to the reusable assembly 128, depleted, discarded and replaced with a new refill assembly 129, at least a portion (i.e., the reusable assembly 128) of the inhaler 100 can be reused with consumable refill assemblies, providing a cost saving benefit. A depleted refill assembly 129 can be recycled. Additionally, refill assemblies 129 of the present disclosure comprising canisters containing different medicaments can be used with the same reusable assembly 128. Therefore, a patient can have several refill assemblies 129, of differing medication, but only require one reusable assembly 128.

In some embodiments, the memory device 125, as shown in FIGS. 2-5 and described in greater detail below, can store information about a medicament canister 114 (see FIG. 3, described below), which can be housed in the refill assembly 129, such as medicament type, expiry date, doses remaining, and the like, and optionally data relating to the usage of the canister 114 (e.g., inhalation profiles for each dose). By providing a memory device 125 in the refill assembly 129, all pertinent information relevant to the canister 114 of a particular refill assembly 129 can remain with the refill assembly 129. As a result, when refill assembly 129 is re-coupled to the reusable assembly 128 (e.g., to re-form the inhaler 100), the above-described relevant information can be accessed by the patient. By way of example, at least some of such information can be shown on a display (e.g., an LCD screen) 1001 (see FIG. 5, described below).

The reusable assembly 128 can further include a Bluetooth module 1008 (see FIG. 5, described below), such that various information (e.g., the usage data) can be shared with a healthcare professional. The usage data can be reviewed by the healthcare professional and used to aid the treatment of the patient's condition(s). Additionally the patient usage experience can be enhanced using the Bluetooth module 1008 to pair the inhaler 100 with another electronic device, e.g., a smart phone with a specific application, or a personal computing device with specific software. Such applications or software can comprise features that aid the patient, for example allowing the patient to review their medicament usage and determine if any doses have been missed when compared with their prescribed dosing regimen.

In some embodiments, it can be important that the refill assembly 129 can only be used when it is coupled with a reusable assembly 128, e.g., to form the inhaler 100. That is, it can be important that the refill assembly 129 has a stand-alone locked state and an unlocked state that can be achieved by coupling the refill assembly 129 to a reusable assembly 128. That can be important for various reasons or can be useful for various scenarios.

For example, if a dose were to be accidentally delivered when the refill assembly 129 was not coupled to a reusable assembly 128 (e.g., during transportation or accidentally when the patient is handling the refill assembly 129), a record of this would not be written to (stored in) the memory device 125 of the refill assembly 129. Therefore, when the refill assembly 129 was subsequently coupled to a reusable assembly 128, the count displayed would be inaccurate, potentially leading to a situation where the patient might run out of medication.

By way of further example, in some embodiments, the reusable assembly 128 includes a breath-actuated dose release firing system (such as a firing system 122 of FIG. 3, described below) and/or a flow governor (such as a flow governor 107 of FIG. 3, described below). In such embodiments, if a patient were able to use the refill assembly 129 (e.g., as a 'press-and-breathe' inhaler) when not coupled to the reusable assembly 128, again an accurate dose count would not be maintained, but additionally the patient would not benefit from the timed delivery resulting from the breath-actuated firing system and/or the medicament being delivered at a governed flow rate, as provided by the reusable assembly 128. Furthermore, as no usage data would be collected regarding time of dosing, inhalation profiles and the like, no usage data would be available for a healthcare professional to review to aid in the management of the patient's condition(s).

FIGS. 3 and 4, which will now be described, show various components of the refill assembly 129 and the reusable assembly 128 of the inhaler 100 in greater detail, by way of example only. As shown in FIG. 3, the inhaler 100, and particularly the reusable assembly 128, can include a reusable air flow path 106 and a flow governor 107 positioned in the reusable air flow path 106.

In some embodiments, the flow governor 107 can be adapted to change its geometry, and thereby its resistance to air flow, as a function of pressure drop between its inlet and its outlet. The flow governor 107 can therefore provide a means of governing the air flow rate (i.e., volumetric flow rate) through the inhaler 100 to reduce inter-patient and intra-patient inhalation variability and provide a more reproducible level of drug deposition in the lung.

By way of example only, in some embodiments, the flow governor 107 can include (i) a tubular element that defines at least a portion of an air flow path therewithin, the tubular element comprising one or more flexible walls configured to flex (or collapse) inwardly in response to an air flow in the air flow path, and (ii) an internal support structure located within the tubular element and configured (e.g., shaped, dimensioned, positioned and having desired material properties) to preserve at least a predetermined cross-sectional area of the air flow path within the tubular element when the one or more flexible walls of the tubular element are flexed (or collapsed) inwardly.

As a result, part of the air flow path cross-sectional area remains open even when the tubular element has collapsed, in order to allow the continued inhalation of air and emitted medicament. A "predetermined cross-sectional area of the air flow path within the tubular element" can include a portion of the air flow path that passes through the internal support structure, e.g., when the internal support structure includes one or more hollow portions or components, as well as a cross-sectional area of space between the tubular element and the internal support structure. The material makeup of the tubular element flexible walls can also be chosen to achieve the desired cross-sectional area between the tubular element and the internal support structure.

Various details regarding flow governors and flow governor assemblies that can be employed in inhalers of the present disclosure, or a portion thereof (such as the reusable assembly 128), can be found in US Application Nos. 62/270,064, 62/270,076, and 62/270,081, filed Dec. 21, 2015, and in US Application Nos. 62/289,651, 62/289,663, and 62/289,676, filed Feb. 1, 2016, each of which is incorporated herein by reference in its entirety.

As further shown in FIG. 3, in some embodiments, the actuator 109 can include a patient port 110 and a stem post 111 with a spray orifice 112 located in the stem post 111. The patient port 110 is shown as being in the form of a mouthpiece that defines an inspiration orifice (or an air outlet). Such a patient port of an inhaler is sometimes referred to herein as a "mouthpiece" for simplicity. However, it should be understood that such patient ports can instead be configured to be nosepieces of nasal inhalers and that the present disclosure can equally apply to nasal inhalers even where not specifically mentioned herein.

As shown in FIG. 3, the refill assembly 129 can include a refill air flow path 113. By way of example only, the refill air flow path 113 is shown as being defined in the refill assembly 129 between the actuator 109 and the air sealing cap 108. The refill air flow path 113 and the reusable air flow path 106 can be connected when the refill assembly 129 and the reusable assembly 128 are coupled together, so that they form an air tight seal. As a result, when suction, i.e., patient inhalation, is applied at the patient port 110, air can only enter through the air inlet 101.

In some embodiments, the inhaler 100, and particularly the refill assembly 129, can include or can be configured to house or employ the medicament canister 114 containing a medicament formulation. By way of example only, the canister 114 is illustrated in FIG. 3 as being a pressurized metered dose inhaler (pMDI) canister, including a valve 115 having a stem 116 that can be seated in the stem post 111 of the actuator 109. The canister 114 is positioned in (e.g., enveloped by) the lockout member 117 and the adapter 118 (see FIGS. 2-4), which can each be dimensioned to receive at least a portion of the canister 114 and can include an annular shape or an annular portion.

As shown in FIGS. 3 and 4, the inhaler 100, or a portion thereof, can include an upper cam linkage 119 (see FIGS. 3 and 4) and the lower cam linkage 120 (see FIGS. 2-4), each of which can be dimensioned to receive at least a portion of the adapter 118 and can include an annular shape or an annular portion. The adapter 118, the upper cam linkage 119, and the lower cam linkage 120 can all be configured to be received within at least a portion of a housing of the reusable assembly 128, within the outer housing 105, and particularly, within at least a portion of an inner housing 121 (see FIGS. 3 and 4) of the reusable assembly 128. The inner housing 121 can also be referred to as an inhaler chassis. The features of the inner housing 121 and the outer housing 105 are described in greater detail below with reference to FIGS. 18-21.

While the housing for the inhaler 100, and particularly, for the reusable assembly 128 is illustrated and described herein as including an inner housing 121 and an outer housing 105, it should be understood that in some embodiments, the housing can be formed of a single piece or part, even if portions of that piece or part are still movable with respect to one another. In addition, while the outer housing 105 is described herein as including a first portion 105a and a second portion 105b, it should be understood that in some embodiments, the outer housing 105 of the reusable assembly 128 can be formed of a single piece or part.

As shown in FIGS. 3 and 4, the inhaler 100, and particularly the reusable assembly 128, can further include a dose release firing system 122. By way of example, the firing system 122 also can include an automatic reset mechanism and/or a damping mechanism. By way of example only, the firing system 122 is shown as including a plunger P that is configured to be operatively coupled to the adapter 118 when the refill assembly 129 is coupled to the reusable assembly 128. The plunger P can be movable (e.g., in the axial direction, e.g., along the axis A) between a first (unfired) position and a second (fired) position that correspond with the first and second positions, respectively, of the adapter 118 (as described below) to cause a dose of medicament to be released.

In some embodiments, the firing system 122 can include a stored energy device (e.g., the stored energy device S of FIGS. 3 and 4) that is configured to drive the adapter 118, either directly, or indirectly (e.g., via the plunger P) from its first position to its second position when the stored energy of the stored energy device is released. In such embodiments, the firing system 122 can be described as being in a primed state when the stored energy is not released and as being in a fired state when the stored energy is released.

In some embodiments, as shown in FIGS. 3 and 4, the stored energy device S can include a biasing element (e.g., a spring), which is shown as a coil spring, and particularly, a compression spring, by way of example only. However, stored energy devices of the present disclosure can include, but are not limited to, one or more biasing elements (e.g., springs), propellants, chemicals, motors, electrical devices, and combinations thereof. In embodiments in which the stored energy device S includes a biasing element, the firing system 122 can be held under load, e.g., against the bias of the biasing element, when in its primed state.

Additional details regarding firing systems and auto-reset firing systems that can be incorporated in reusable assemblies and/or inhalers of the present disclosure can be found in US Application Nos. 62/270,066 and 62/270,070, both of which were filed on Dec. 21, 2015, and each of which is incorporated herein by reference in its entirety. Other firing systems or auto-reset firing systems can also be employed in the reusable assemblies and/or inhalers of the present disclosure.

Figure 5:
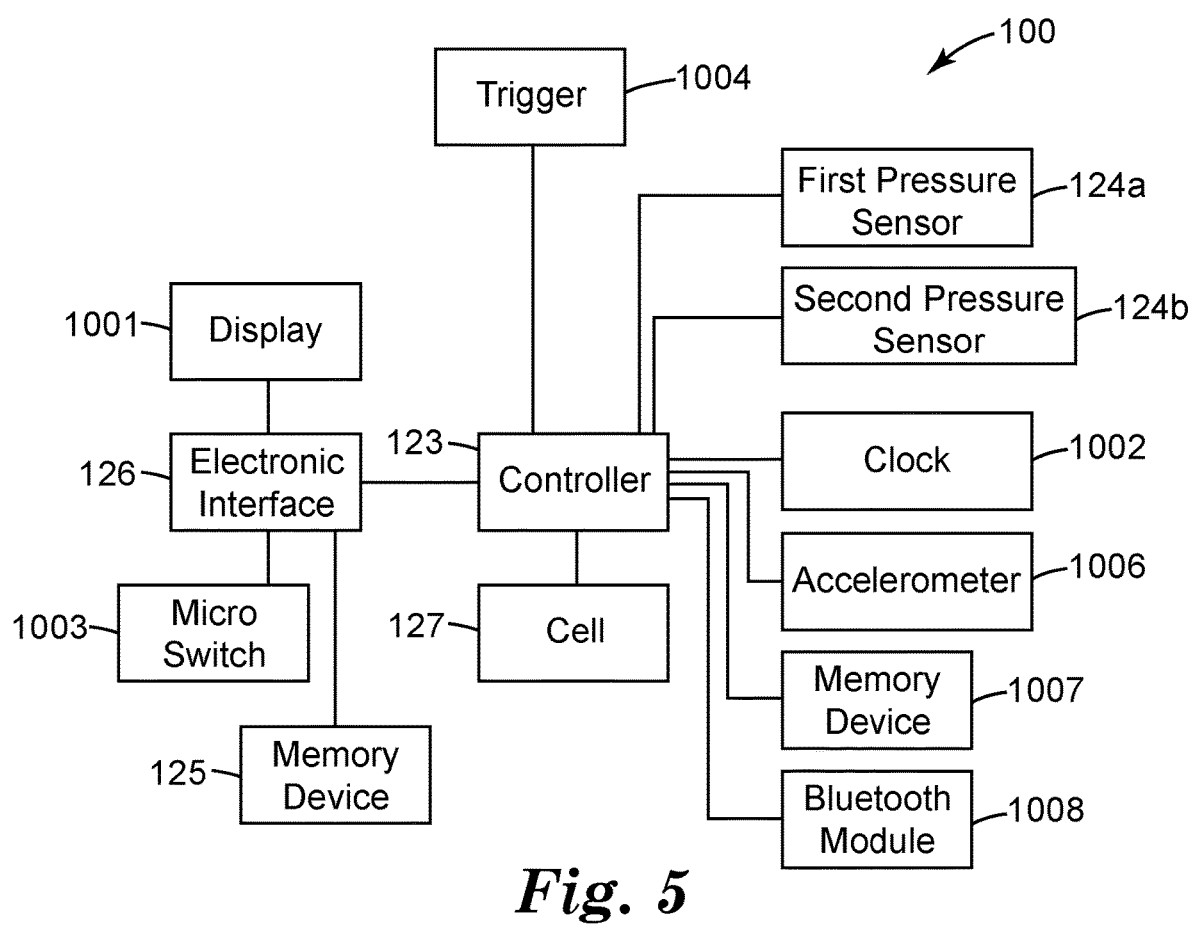
FIG. 5 is a schematic block diagram of the inhaler of FIGS. 1-4.

As shown in FIGS. 3 and 4, in some embodiments, the inhaler 100, or a portion thereof, can include a controller 123, and one or more pressure sensors. Two pressure sensors 124a and 124b are shown in FIG. 5 by way of example. As shown in FIG. 3, in such embodiments, a first pressure sensor 124a can be located above, i.e., upstream of, the flow governor 107, and a second pressure sensor 124b (not visible in the cross-sectional view of FIG. 3) located below, i.e., downstream of, the flow governor 107. Particularly, in some embodiments, the second pressure sensor 124b can be located below the level of the memory device 125 of FIG. 3, and can be located in the actuator 109 of the refill assembly 129. In some embodiments, the combination of the flow governor 107, along with the one or more pressure sensors 124, can be referred to as a flow governor assembly.

As shown in FIG. 4, the memory device 125 can connect to an electronic interface 126, to which the control button 103 and the display 1001 can also connect. In some embodiments, the display 1001 can include a liquid crystal display (LCD) screen. The electronic interface 126 can also be connected to a controller 123, e.g., via an electrical conduit 1002, as shown in FIG. 4. Power can be supplied from an on-board power supply, such as a cell 127 (see FIG. 4), which can be connected to the controller 123.

Generally, the controller 123 can be a suitable electronic device, such as, for example, a programmable logic controller ("PLC"), a microprocessor, or the like. As such, the controller 123 may include both hardware and software components, and the term "controller" is meant to broadly encompass the combination of such components.

As shown in FIG. 5, the cell 127 can be connected to the controller 123 and can provide power for all of the electronic components of the inhaler 100, or a portion thereof, which can be regulated by the controller 123. In some embodiments, as further shown in FIG. 5 by way of example, the controller 123 can include or be associated with one or more of a clock 1002, an accelerometer 1006, a memory device 1007, and a Bluetooth module 1008. The controller 123 can also be connected to the first and second pressure sensors 124a and 124b, a trigger (or triggering system, or triggering element) 1004 (e.g., an electronic trigger) for the firing system 122, and the electronic interface 126. In addition, the display 1001, a micro switch 1003, and the memory device 125 (e.g., located in the refill assembly 129 of the embodiment of FIGS. 1-6), can be connected to the electronic interface 126. As mentioned above, in some embodiments, the Bluetooth module 1008 can be located in, or form a portion of, the reusable assembly 128, and the Bluetooth module 1008 can enable sharing of various information (e.g., the usage data of the inhaler 100) with a healthcare professional.

Use of the inhaler 100 will now be described with reference to FIGS. 3-5. In some embodiments, when the patient opens the patient port cover 104 (as described in greater detail below with respect to FIG. 6), this can activate the micro switch 1003, which can communicate with the controller 123 to permit power to flow to the other electronic components. The micro switch 1003 can be positioned so that it is triggered by movement of the patient port cover 104 and/or by movement of the upper cam linkage 119. In the latter case, the micro switch 1003 can be connected directly to the controller 123. Alternatively, the patient can press the control button 103, which can interact with the electronic interface 126 to power up the other electronics, and can then open the patient port cover 104. With the patient port cover 104 open, the patient can position at least a portion of the patient port 110 within their nose or mouth and inhale. This inhalation causes air to flow in through the air inlet 101, through the reusable air flow path 106, through the flow governor 107, through the refill air flow path 113, around the stem post 111 and past the spray orifice 112, resulting in the air exiting from the patient port 110 into the patient.

The flow of air results in a pressure change, e.g., sensed by the pressure sensors 124a and 124b which communicate with the controller 123. When the appropriate flow rate is achieved, the controller 123 directs power from the cell 127 to the trigger 1004, which activates the firing system 122, causing it to fire. In some embodiments, the trigger 1004 can include at least one of a shape memory alloy, a digital motor, an electromagnet, a solenoid, or a combination thereof. Additional details and configurations of examples of various triggers that can be employed in the reusable assemblies and/or inhalers of the present disclosure are described in U.S. Application No. 62/270,066, filed Dec. 21, 2015, which is incorporated herein by reference in its entirety.

In some embodiments, the controller 123 and the pressure sensors 124a, 124b can form at least a portion of an inspiratory air flow detection system that can provide an electrical signal that is used to activate the trigger 1004 to trigger the firing system 122 to cause a dose of medicament to be released according to a defined algorithm.

Force can be transferred from the firing system 122 to the adapter 118. In some embodiments employing a breath-actuated pMDI, and particularly, an electronic (or electronically triggered) breath-actuated pMDI, the inhaler 100 can further include the firing system 122 (e.g., the breath-actuated firing system) in combination with the inspiratory air flow detection system. In such embodiments, the firing system 122 can provide sufficient force to actuate the canister valve 115, i.e., to move the canister 114 downwards relative to the valve stem 116 to release (i.e., dispense) a dose of medicament from the spray orifice 112. The dose can be received by the patient via the patient port 110.

During this inspiratory process, the flow governor 107 can ensure that inhalation is governed to within a desired range of flow rates. After delivery of the dose, the firing system 122 can function to allow the canister 114 to return to its rest position. The controller 123 can communicate with the memory device 125, such that data are written to the memory device 125 indicating that a dose has been delivered. The inhaler 100 can also be capable of capturing other data, such as the patient's inhalation profile and the time/date that the dose was taken, e.g., as derived from the clock 1002.

Additionally, the presence of the accelerometer 1006 (e.g., a three-axis accelerometer) can allow capture of data relating to the force and duration of the shake performed by the patient prior to taking a dose of medicament and the orientation of the inhaler 100 during medicament dosing. These data can also be written to the memory device 125 of the refill assembly 129 and/or can be written to the memory device 1007 associated with the controller 123 (see FIG. 5).

Furthermore, the display 1001 can show the number of doses remaining in the canister 114, so that the patient can be informed and can obtain more medication if necessary. The display 1001 may also inform the patient that another dose is required, depending on the type of medication being taken, and/or can instruct the patient that they have taken the sufficient number of doses. After the patient has completed taking their medication, the patient can close the patient port cover 104.

Figure 6:
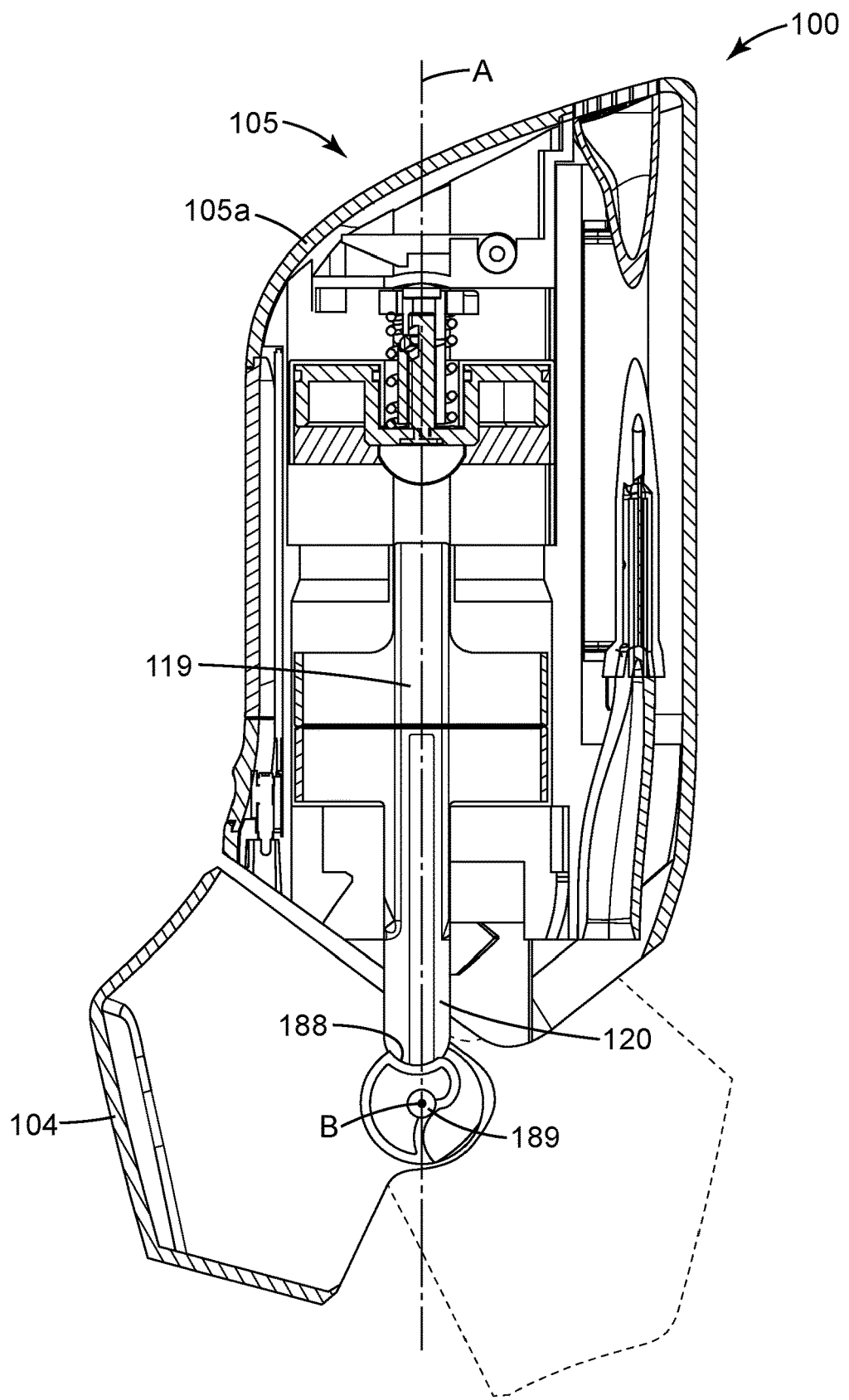
FIG. 6 is a side cross-sectional view of the inhaler of FIGS. 1-5.

As shown in FIG. 6, in some embodiments, the patient port cover 104 can be movable between an open position (shown in dashed lines in FIG. 6) and a closed position by pivoting about a pivot axis B. That is, the action of closing the patient port cover 104 can result in one or more cams 188 (described in greater detail below with respect to FIG. 14) on the patient port cover 104 interacting with the lower cam linkage 120, causing it to travel (e.g., axially, e.g., along or parallel to the axis A), which in turn acts on the upper cam linkage 119, and through their travel (e.g., axial travel), guided by the inner housing 121, the firing system 122 can be reset. As described above, the firing system 122 can include a plunger P (see FIGS. 3 and 4) that is movable between a first (unfired) position and a second (fired) position, and movement of the patient port cover 104 to its closed position can return the plunger P to its starting or unfired position. The inhaler 100 is now ready for the patient to take their next dose when required. In some embodiments, closing of the patient port cover 104 can also signal the electronic components to power down, the prompt for which can come from the patient port cover 104 triggering the micro switch 1003.

Figure 7:
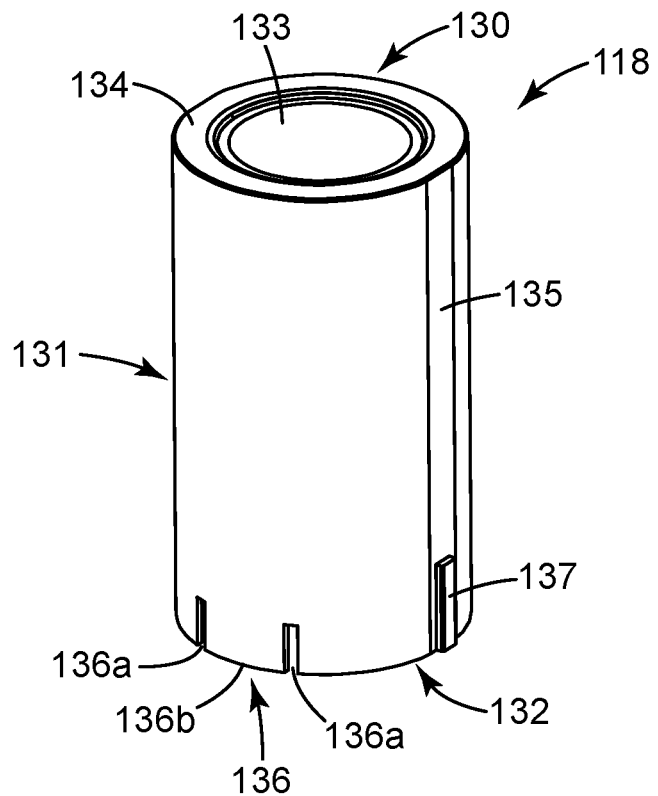
FIG. 7 is a front isometric view of the adapter of the refill assembly of FIG. 2.
Figure 8:
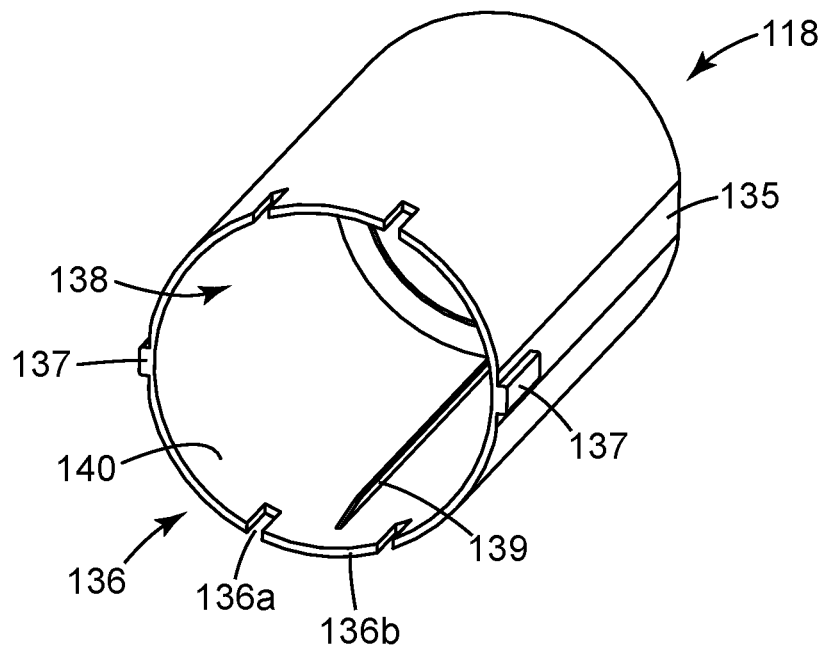
FIG. 8 is a bottom isometric view of the adapter of FIG. 7.

FIGS. 7 and 8 illustrate the adapter 118 in greater detail. Referring to FIG. 7, the adapter 118 has a generally cylindrical shape, including a top section 130, a body section 131 and a bottom section 132. As shown, the top section 131 can include an inner recessed (e.g., circular) section 133 and an outer section 134 that is predominantly circular with the exception of a pair of flat portions, edges or sections 135 on opposite sides that extend down the body section 131. The inner section 133 is recessed from the outer section 134 and exists in a slightly lower plane. When present in the inhaler 100, the top section 131 is positioned to be in contact with the firing system 122, as shown in FIG. 3. The bottom section 132 can also be generally circular, as shown in FIG. 8. As shown, the adapter 118 can include one or more first engagement features 136 (e.g., in the bottom section 132), which are shaped and positioned to engage one or more second engagement features of the lockout member 117, as described in greater detail below.

Throughout the present disclosure, the phrase "engagement feature" and variations thereof is used to represent a feature that is shaped and configured to engage with another mating or corresponding engagement feature, typically of another part or component. In some cases in the present disclosure, such an engagement feature may be described as a post or a projection that is dimensioned to be received in a recess or socket, e.g., of another component. However, it should be understood that even though a first part may be illustrated and described herein as including the post and a second mating part may be described as including the recess, the opposite configuration (e.g., where the first part includes the recess and the second mating part includes the post) can also be employed and is within the spirit and scope of the present disclosure.

By way of example only, the first engagement features 136 of the adapter 118 include two sets of two lockout recesses 136a and two projections 136b, each projection 136b being defined by the cylindrical wall of the adapter 118 that is located between two spaced-apart (i.e., circumferentially spaced, e.g., with respect to the axial direction) lockout recesses 136a. As shown in FIG. 8, the adapter 118 includes a pair of lockout recesses 136a and a projection 136b on either side of adapter 118 (e.g., such that the first engagement features 136 include two diametrically opposed sets of recesses 136a and projection 136b). The transverse, cross-sectional shape of the body section 131 is substantially circular, with the exception of the flat portions 135. At the bottom of the flat portions 135 (e.g., adjacent a bottom edge of the bottom section 132) is a guide 137 having a rectangular shape by way of example. A further guide 137 is present on the opposite side of the adapter 118 (e.g., such that one flat portion 135 and associated guide 137 is diametrically opposed from the other flat portion 135 and guide 137). Both guides 137 are visible in FIG. 8.

As further shown in FIG. 8, in some embodiments, the adapter 118 can further include an inner chamber 138 dimensioned to receive the canister 114, as shown is FIG. 3, with a rib 139 located on an inner surface 140 of the adapter 118. In some embodiments, the rib 139 can extend from the top of adapter 118 and can terminate with a tapered end above a closed end of the lockout recesses 136a, as shown in FIG. 8. Two further ribs can exist on the inner surface 140 of the adapter 118, and by way of example, can all be equally spaced circumferentially (e.g., with respect to the axial direction) about the inner surface 140. The purpose of the one or more ribs, and particularly, three ribs 139, is to ensure a tight fit of the canister 114 when inserted into the inner chamber 138 of the adapter 118 and to inhibit lateral movement of the canister 114 in the adapter 118.

In some embodiments, as shown in FIGS. 7-8, the adapter 118 can be formed of a material that is substantially not transparent (or is opaque), such that when the canister 114 is positioned in the inner chamber 138 of the adapter 118, the canister 114 is not visible to the patient. However, it should be understood that the adapter 118 can instead be constructed using a transparent material so that the patient is able to see any labeling on the canister 114. Alternatively, in some embodiments, the adapter 118 can include at least a transparent portion (e.g., a window) through which the patient can view any labeling on the canister 114 (at least when the refill assembly 129 is not coupled to the reusable assembly 128).

As described above, movement of the adapter 118 can cause a dose of medicament to be released, e.g., from the patient port 110. That is, the adapter 118 can be movable (e.g., in the axial direction) between a first position (e.g., a first axial position) in which a dose of medicament is not released and a second position (e.g., a second axial position) in which a dose of medicament is released. The lockout member 117, which is shown in greater detail in FIGS. 9-11 and described below, can be configured to lock the adapter 118 in its first position, thereby locking the refill assembly 129, particularly when the refill assembly 129 is not coupled to a reusable assembly 128.

That is, the lockout member 117 can be movable between (i) a first position (e.g., relative to the adapter; see FIG. 16, described below) in which the adapter is not movable (e.g., relative to the lockout member) from its first position to its second position, i.e., is locked, and (ii) a second position (e.g., relative to the adapter; see FIG. 23, described below) in which the adapter is movable (e.g., relative to the lockout member) from its first position to its second position, i.e., is unlocked. When the refill assembly 129 is not coupled to a reusable assembly, the lockout member 117 is in its first position (e.g., can be biased in its first position). Coupling the refill assembly to a reusable assembly can cause the lockout member 117 to move to its second position, thereby unlocking the adapter 118 and allowing the adapter 118 to be moved to its second position to release a dose of medicament. In some embodiments, when the lockout member 117 is in its first position, the adapter 118 may be at least somewhat movable, however, the adapter 118 is not fully movable from its first position to its second position to cause a dose of medicament to be released, even if some slight movement out of its first position is possible.

In some embodiments, the lockout member 117 can be rotatable between its first position and its second position. In some embodiments, the lockout member 117 can be rotatable (e.g., about the axial direction, e.g., about the axis A) and/or translatable (e.g., in the axial direction) between its first position and its second position.

Figure 9:
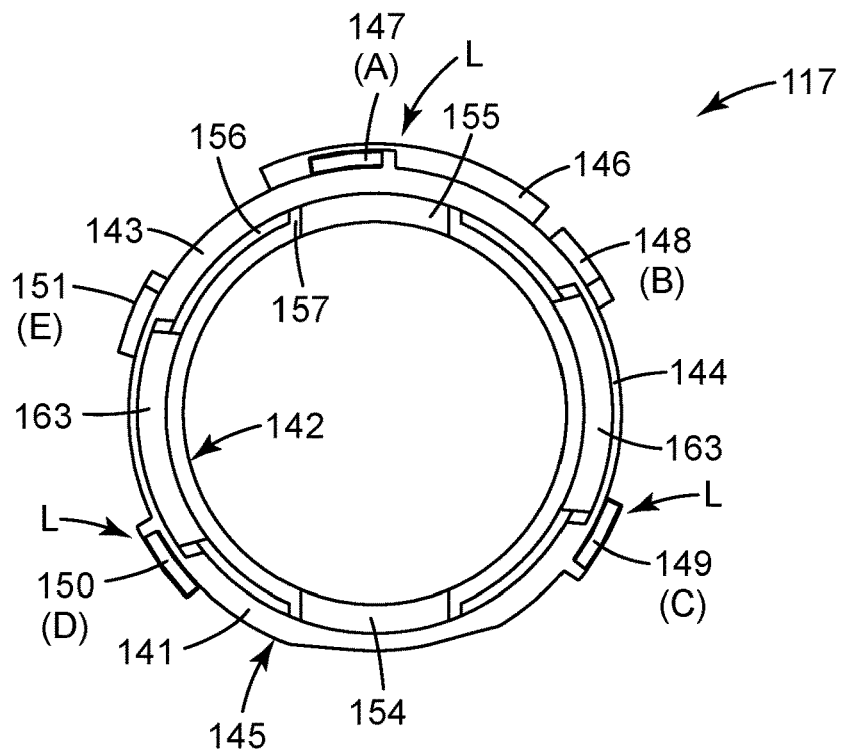
FIG. 9 is a top plan view of the lockout member of the refill assembly of FIG. 2.
Figure 10:
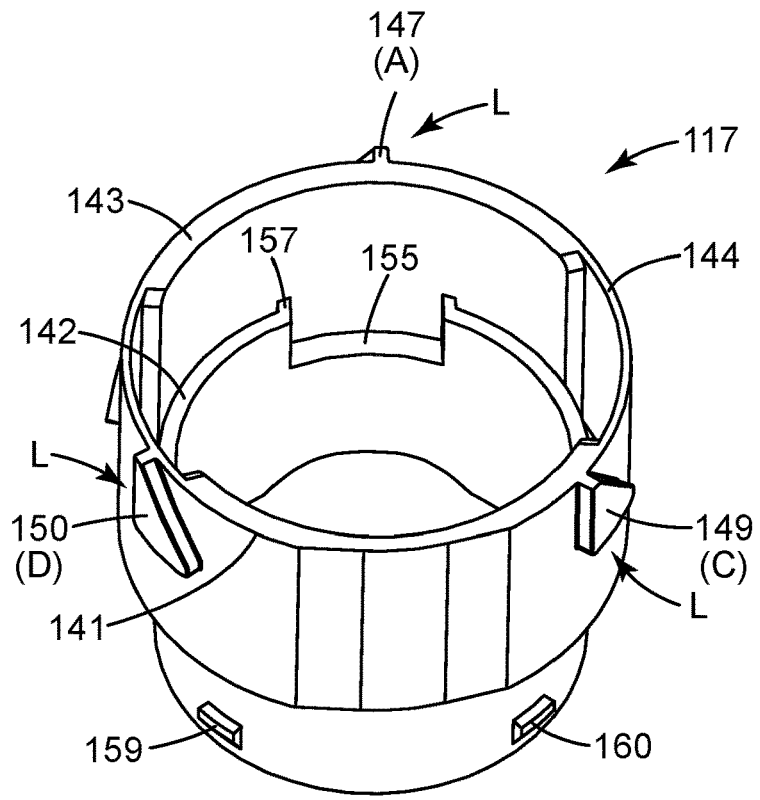
FIG. 10 is a front isometric view of the lockout member of FIG. 9.
Figure 11:
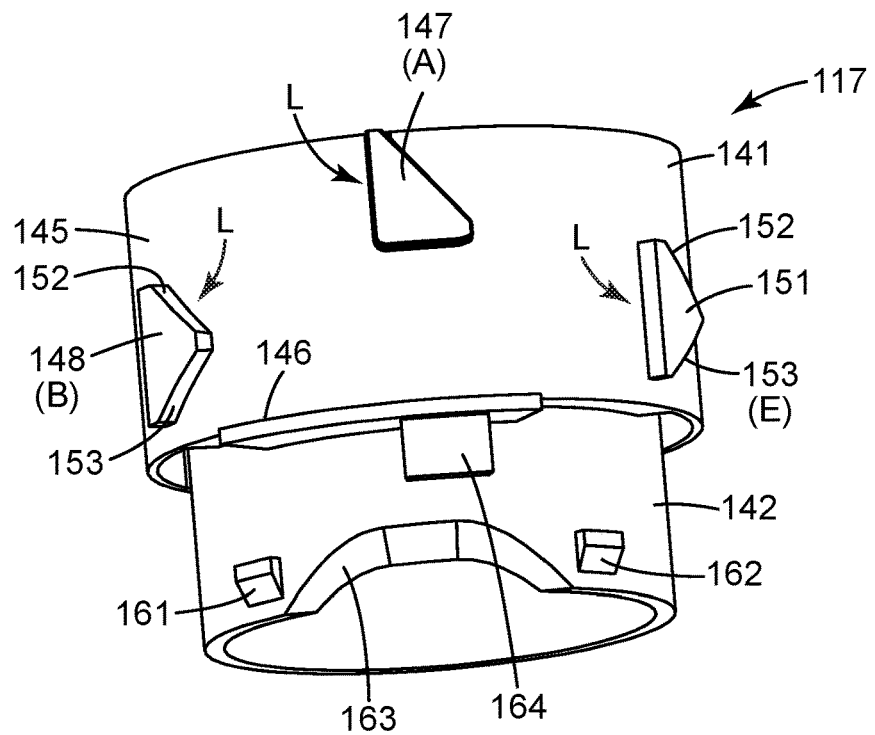
FIG. 11 is a rear isometric view of the lockout member of FIGS. 9-10.

As shown in FIGS. 9-11, the lockout member 117 of the illustrated embodiment is in the form of, or includes, a lockout collar that is generally annular in shape. As shown, in some embodiments, such a lockout collar can be dimensioned to receive at least a portion of the adapter 118. By way of example only, the lockout member 117 generally has the form of two coupled (e.g., interconnected) hollow cylinders—an outer top cylinder 141 and an inner bottom cylinder 142. The outer top cylinder 141 has a greater diameter than the inner bottom cylinder 142, and the inner bottom cylinder 142 is partially enveloped by the outer top cylinder 141, as shown in FIGS. 10 and 11. With reference to FIG. 9, it can be seen that the outer top cylinder 141 can include a thick wall section 143, a thin wall section 144, and an outer ledge 146 that extends outwardly (e.g., radially outwardly) from an external surface 145 of the outer top cylinder 141. As shown in FIG. 11, the outer ledge 146 is located adjacent the base of the outer top cylinder 141.

As shown in FIGS. 10 and 11, the lockout member 117 can further include one or more first lockout engagement features L, which are configured to engage with at least a portion of the reusable assembly 128 (e.g., second lockout engagement features L', as shown in FIGS. 18-21 and described below) to move the lockout member 117 from its first position in which the lockout member 117 is positioned to inhibit movement of the adapter 118 to release a dose of medicament to its second position in which the lockout member 117 does not inhibit movement of the adapter 118 from its first position to its second position (and the adapter 118 is free to move between its first position and its second position).

The first lockout engagement features L of the lockout member 117 of the illustrated embodiment include a plurality of posts (or projections, or protrusions), e.g., teeth, located on the external surface 145 of the outer top cylinder 141. Each post extends generally radially outwardly from the external surface 145 of the outer top cylinder 141. By way of example, the posts are referred to herein as "teeth" and each post as a "tooth," however, it should be understand that other terms can be used to described the radially projecting posts, such as simply posts or projections. By way of example only, the posts (e.g., teeth) include tooth A 147, tooth B 148, tooth C 149, tooth D 150 and tooth E 151. Tooth A 147, tooth B 148 and tooth E 151 are located towards the rear of the lockout member 117 and are visible in FIG. 11, and tooth C 149 and tooth D 150 are located towards the front of lockout member 117 and are visible in FIG. 10.

Referring to FIG. 10, it can be seen that the top of tooth A 147, tooth C 149 and tooth D 150 are flat and flush with a top surface of the outer top cylinder 141, whereas tooth B 148 and tooth E 151 are located lower down on the external surface 145 of the outer top cylinder 141, as shown in FIG. 11. Furthermore, as shown in FIGS. 10 and 11, it can be seen that the shape of tooth B 148 and tooth E 151 differs from that of tooth A 147, tooth C 149 and tooth D 150. Tooth A 147, tooth C 149 and tooth D 150 are shown by way of example as having the shape of a scalene triangle, whereas tooth B 148 and tooth E 151 each generally have the shape of an isosceles triangle, with a sloped top edge 152 and sloped bottom edge 153. Additionally, it should be noted that although tooth A 147, tooth B 148, tooth C 149, tooth D 150 and tooth E 151 are described as generally having a triangular shape, flat sections are present at two of the vertices for tooth A 147 tooth C 149 and tooth D 150, and flat sections exist at all three vertices of tooth D 150 and Tooth E 151.

While the above-described posts, i.e., teeth, of the present embodiment are shown as described as being triangular, it should be understood that other shapes of lockout engagement features are possible without departing from the spirit and scope of the present disclosure. The mating lockout engagement features can be altered accordingly to engage with non-triangular shaped features.

Referring to FIGS. 9 and 10, the top section of the inner bottom cylinder 142 is not continuous, creating a curved (circumferential) front recess 154 and an opposing (i.e., diametrically opposed) curved (circumferential) rear recess 155, each of which is recessed axially (in the axial direction), i.e., downwardly from a top surface or edge of the inner bottom cylinder 142.

As shown in FIG. 9, as a result of the inner bottom cylinder 142 having a smaller external diameter than the inner diameter of outer top cylinder 141, and the inner bottom cylinder 142 being enveloped by the outer top cylinder 141, an enclosed curved (circumferential) recess 156 is formed on each side of the lockout member 117 between the outer top cylinder 141 and the inner bottom cylinder 142. Each enclosed recess 156 extends from a first circumferential location at which the inner bottom cylinder 142 meets the outer top cylinder 141 to a second circumferential position where the thick walled section 143 of the outer top cylinder 141 ends. The enclosed recesses 156 can each be dimensioned to receive at least a portion of the adapter 118 (e.g., at least a portion of the bottom section 132 of the adapter 118).

Figure 23:
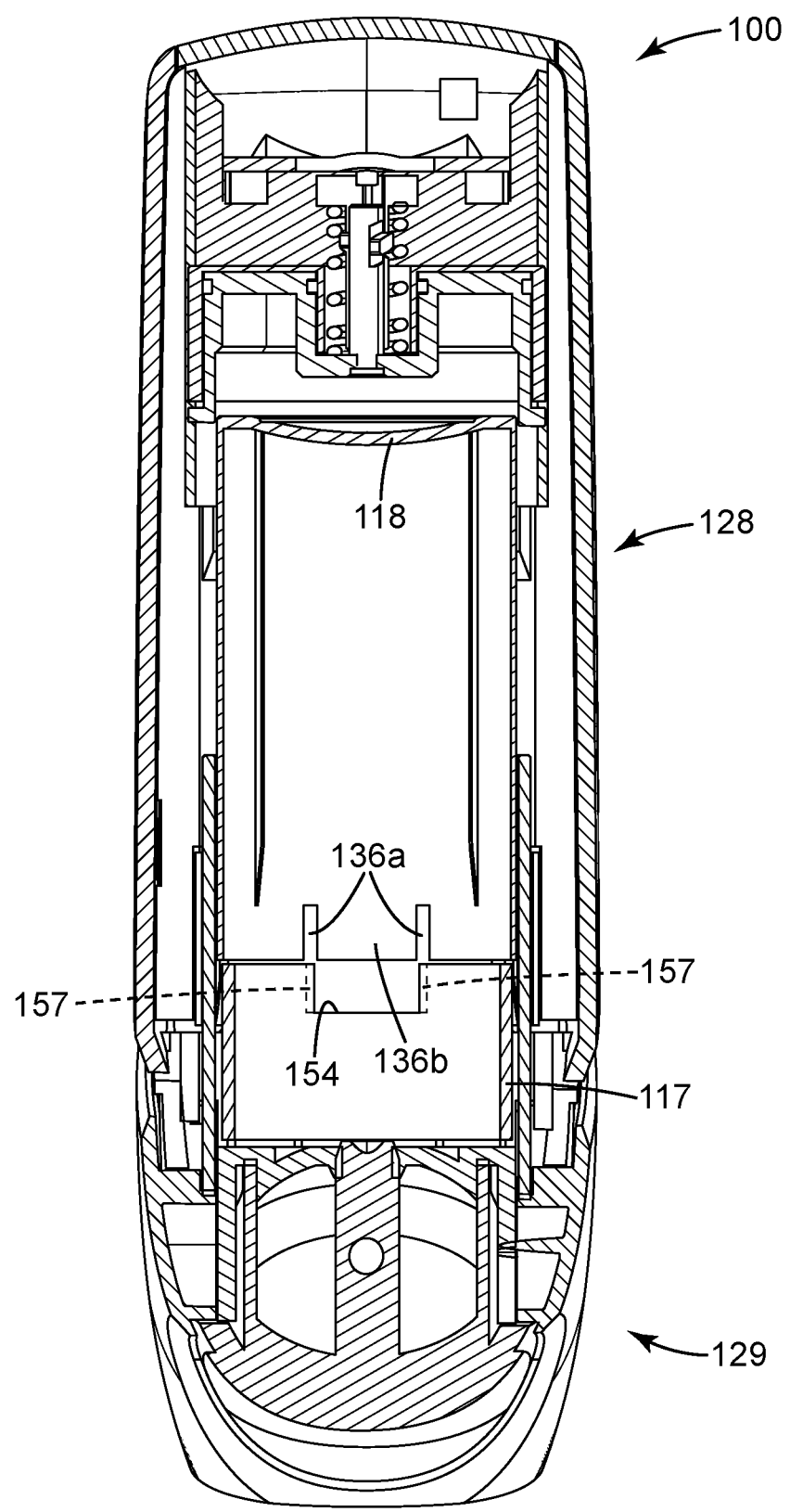
FIG. 23 is a rear cross-sectional view of the inhaler of FIGS. 1-4, with portions removed for clarity, and with the lockout member of FIGS. 9-11 in its second (unlocked) position.

The front recess 154 and the rear recess 155 are separated from their neighboring enclosed recesses 156 by ribs 157 (see FIGS. 9 and 10) that each extend at least partially radially from the inner bottom cylinder 142 to an inner surface of the outer top cylinder 141, and that each also form a connection between the inner bottom cylinder 142 to the outer top cylinder 141. Each recess 154 and 155 is dimensioned to receive a projection 136b of the adapter 118, and each lockout recess 136a of the adapter 118 is dimensioned to receive at least a portion of a rib 157 of the lockout member 117 and to allow for relative movement (e.g., relative axial movement, in the axial direction) between the adapter 118 and the lockout member 117, i.e., when the lockout member 117 is in its second position, as shown in FIG. 23 and described below. As a result, the recesses 154, 155 and the ribs 157 form second engagement features that are configured to engage the first engagement features of the adapter 118. The first engagement features and the second engagement features are shown by way of example only and other inter-engaging features can be employed on the adapter 118 and/or the lockout member 117 that allow for relative (e.g., axial) movement between the adapter 118 and the lockout member 117 but which require alignment (e.g., rotational alignment) therebetween in order to engage and provide the relative movement.

As shown in FIG. 9, the lockout member 117 can further include a pair of curved (circumferential) receiving slots 163 (e.g., two, diametrically opposed slots 163), each created between the inner bottom cylinder 142 and the thin wall section 144 of the outer top cylinder 141.

With continued reference to FIGS. 10 and 11, the lockout member 117 can further include additional engagement features for coupling the lockout member 117 to another portion of the refill assembly 129, such as the air sealing cap 108, as described below. By way of example, the additional engagement features are located toward the bottom of an external surface of the inner bottom cylinder 142. By way of further example, the engagement features can include a wedge A 159, a wedge B 160, a wedge C 161 and a wedge D 162. Wedge A 159 and wedge B 160 are located at the front of the inner bottom cylinder 142, and wedge C 161 and wedge D 162 are located at the rear of the inner bottom cylinder 142.

As shown in FIG. 11, in some embodiments, the lockout member 117 can further include a curved angled surface 163 located between the wedge C 161 and the wedge D 162. The curved angled surface 163 can accommodate the profile of the air sealing cap 108 when the refill assembly 129 is assembled. In addition, as shown in FIG. 11, the lockout member 117 can include a guide 164 that extends from the lower surface of the outer ledge 146 but which is spaced outwardly from the external surface of the inner bottom cylinder 142.

Figure 12:
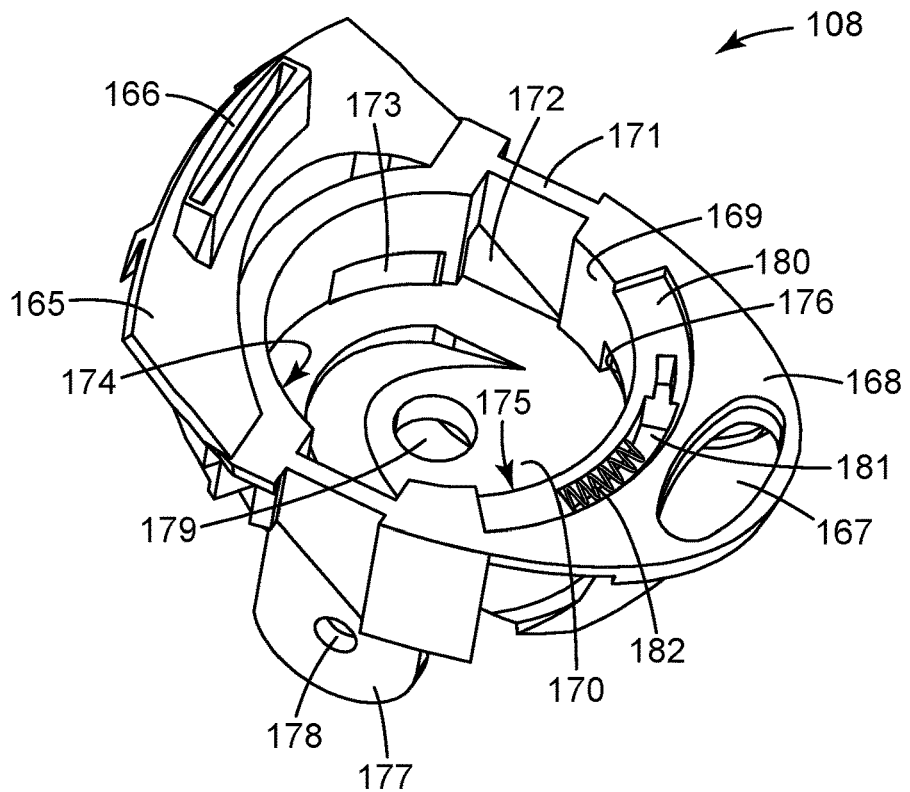
FIG. 12 is an isometric view of the air sealing cap of the refill assembly of FIG. 2.

The air sealing cap 108 is shown in greater detail in FIG. 12. At the front of the air sealing cap 108 is a curved banked surface or section 165, in the middle of which a memory device housing 166 is located. Towards the back of the air sealing cap 108 is a refill air flow path inlet 167. As shown, the air sealing cap 108 can further include a flat surface 168 that can connect the refill air flow path inlet 167 with the banked surface 165. A wall 169 can connect the flat surface 168 with a base 170. The air sealing cap 108 can further include a pair of thin walls 171 located on opposite sides of the air sealing cap 108 and that are each spaced outwardly from the base 170 to form a receiving slot 172 between the base and the thin wall 171. The wall 169 of the air sealing cap 108 can include (e.g., toward the base 170) one or more wedge guides, each dimensioned to receive a wedge of the lockout member 117, described above.

By way of example only, in some embodiments, the wedge guides can include a wedge guide A 173, a wedge guide B 174, a wedge guide C 175, and a wedge guide D 176. The wedge guides B 174 and C 175 are located on one side of the air sealing cap 108 where they are not visible in FIG. 11, but their locations are indicated. Extending down from the base 170 is a pair of arms 177, one on each opposing side (a second arm 177 is not visible in FIG. 12). Each arm 177 can include a cam axle receiver 178 (e.g., in the form of an aperture) located toward the bottom of the arm 177. The base 170 can include a stem socket receiver 179 (e.g., in the form of an aperture), located approximately centrally in the base 170. Furthermore, in some embodiments, as shown, the air sealing cap 108 can include an outer ledge recess 180 which can extend substantially circumferentially with respect to the axial direction (e.g., with respect to the axis A) and therefore has a curved shape. The outer ledge recess 180 includes a guide housing 181. The outer ledge recess 180 and the guide housing 181 are dimensioned to receive the outer ledge 146 and the guide 164 of the lockout member 117, respectively, when the lockout member 117 and the air sealing cap 108 are coupled together, as described in greater detail below. A biasing element 182 (e.g., a spring), which is shown as a coil spring, and particularly, a compression spring, by way of example only, can be located within the guide housing 181.

Figure 13:
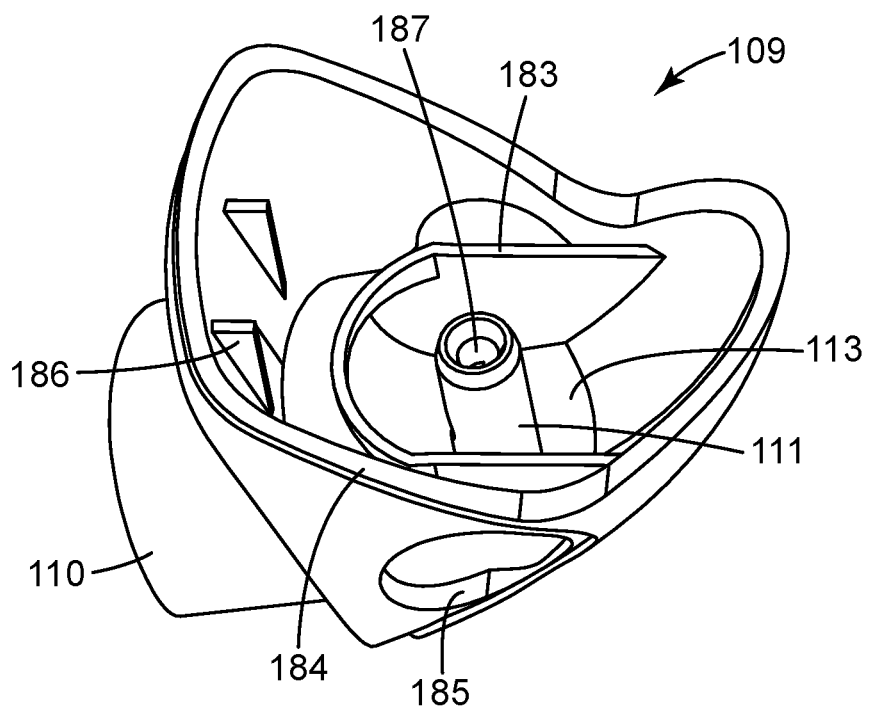
FIG. 13 is an isometric view of the actuator of the refill assembly of FIG. 2.

The actuator 109 is shown in greater detail in FIG. 13. As shown in FIG. 13, in some embodiments, the actuator 109 can include an inner section or portion 183 and an outer section or portion 184, as well as the patient port 110. In some embodiments, the actuator 109 can be formed of one single part or piece, such that the patient port 110 is integrally formed with the inner section 183 and the outer section 184. Each side of the actuator 109 of the illustrated embodiment includes a cam guide 185 and a support wedge 186, such that the actuator 109 includes a pair of opposing cam guides 185 (one on each opposing side of the actuator 109) and a pair of support wedges 186. The support wedges 186 are located on an inner surface of the outer section 184 and are positioned to support the memory device 125. At least a portion of the actuator (e.g., the inner section 183) can be configured to define at least a portion of the refill air flow path 113. The stem post 111 is located in the inner section 183 of the actuator and includes at its top, a stem socket 187. The actuator 109 is configured to receive at least a portion of the air sealing cap 108. That is, the general profile of the actuator 109 is shaped and sized such that it can receive the air sealing cap 108.

In some embodiments, the actuator 109 can be described as a housing, or an outer housing, of the refill assembly 129 that also includes or defines the patient port 110. In addition, such a housing can be described as being dimensioned to receive and be coupled to (e.g., directly, or indirectly, e.g., via the air sealing cap 108) at least a portion of the lockout member 117. In some embodiments, the housing can be described as being dimensioned to receive at least a portion of the air sealing cap 108, which can also be referred to as an inner housing of the refill assembly 129, and the air sealing cap, or inner housing, 108 can be dimensioned to receive at least a portion of the lockout member 117.

Figure 14:
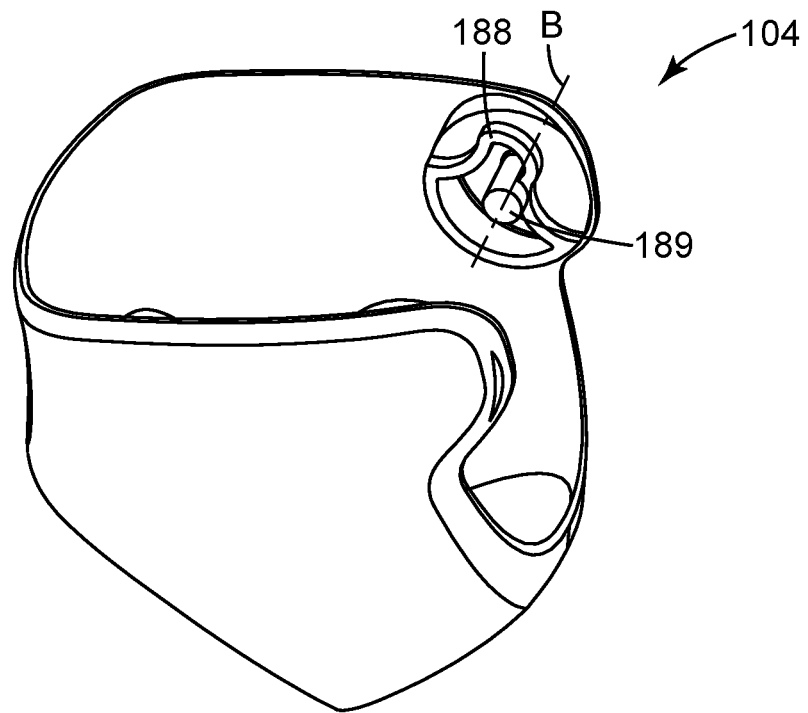
FIG. 14 is a side isometric view of the patient port cover of the refill assembly of FIG. 2.

FIG. 14 shows the patient port cover 104 in greater detail. As mentioned above, in some embodiments, the patient port cover 104 can be pivotally movable about a pivot axis B. In some embodiments, the pivot axis B can be oriented substantially perpendicularly with respect to the axis A of the refill assembly 129 (or the inhaler 100). In some embodiments, as shown in FIGS. 6 and 14, the patient port cover 104 can include a cam 188 about an axle 189 (e.g., one on each side, such that the cover 104 includes two cams 188 and two axles 189, only one of each being visible in FIGS. 6 and 14). The axle 189 extends along and defines the pivot axis B. The patient port cover 104 can be dimensioned to receive (i.e., to cover) the patient port 110 and to house or enclose at least a portion of the contour of the front of the outer section 184 of the actuator 109, i.e., when in its closed position (see FIG. 6).

Figure 15:
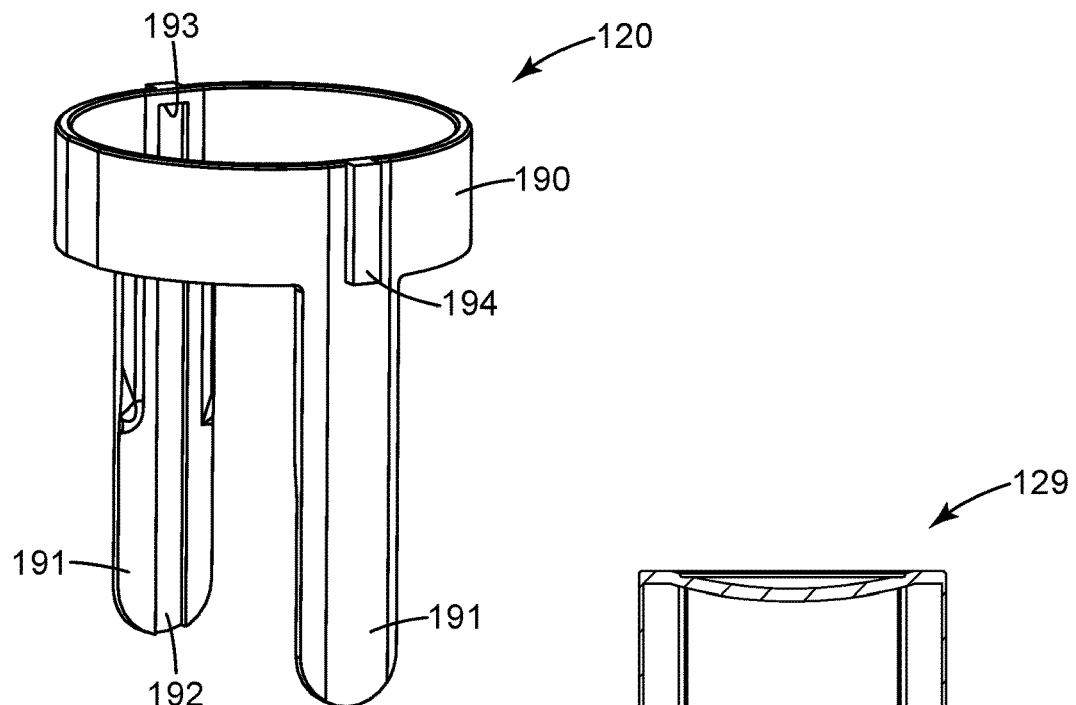
FIG. 15 is a side isometric view of the lower cam linkage of the refill assembly of FIG. 2.

FIG. 15 shows the lower cam linkage 120 in greater detail. As shown in FIG. 15, in the illustrated embodiment, the lower cam linkage 120 can include an annular collar 190 from which a pair of arms 191 (e.g., diametrically opposed arms 191) extends axially (e.g., axially downwardly). The inner surface of each arm 191 can include a guide recess 192 that extends axially. Each guide recess 192 is shown as being open-ended on one end (e.g., at the bottom of each arm 191) and closed on the opposite end, forming a guide recess stop 193. In addition, the lower cam linkage 120 can further include a pair of guides 194 (one on each side) that are located on an outer surface of the collar 190, each centrally aligned with an arm 191. The guides 194 are illustrated as having a rectangular shape by way of example with a longer axis that is generally aligned in the axial direction and is oriented axially with respect to the arms 191.

Assembly of the refill assembly 129 and the interaction of each part will now be described, with reference to FIGS. 2-4 and 6-15. In some embodiments, as shown, the air sealing cap 108 can be received by the actuator 109, and the memory device 125 can be received in the memory device housing 166 of the air sealing cap 108. The stem post 111 of the actuator 109 can be received by the stem post receiver 179 of the air sealing cap 108, and each arm 177 of the air sealing cap 108 can be located in alignment with a cam guide 185 of the actuator 109. In some embodiments, the air sealing cap 108 and the actuator 109 can be permanently coupled together after being assembled, for example by ultrasonic welding.

A variety of coupling means can be employed to allow the respective components of the refill assembly 129 or the reusable assembly 128 to be removably coupled to one another, including, but not limited to screw threads, press-fit engagement (also sometimes referred to as "friction-fit engagement" or "interference-fit engagement"), snap-fit engagement, magnets, hook-and-loop fasteners, adhesives, cohesives, clamps, heat sealing, other suitable removable coupling means, and combinations thereof. In some embodiments, the components of each of the refill assembly 129 and the reusable assembly 128 can be permanently or semi-permanently coupled to one another. Such permanent or semi-permanent coupling means can include, but are not limited to, adhesives, stitches, staples, screws, nails, rivets, brads, crimps, welding (e.g., sonic (e.g., ultrasonic) welding), any thermal bonding technique (e.g., heat and/or pressure applied to one or both of the components to be coupled), snap-fit engagement, press-fit engagement, heat sealing, other suitable permanent or semi-permanent coupling means, and combinations thereof. One of ordinary skill in the art will recognize that some of the permanent or semi-permanent coupling means can also be adapted to be removable, and vice versa, and are categorized in this way by way of example only.

In embodiments in which the air sealing cap 108 and the actuator 109 are permanently coupled together, the memory device 125 cannot be removed without breaking or otherwise causing destruction to the refill assembly 129. Furthermore, in such embodiments, when air is inhaled from the patient port 110, air can only flow in via the refill air flow path inlet 167, as shown in FIG. 12.

By way of example only, the inner bottom cylinder 142 of the lockout member 117 can be coupled to the air sealing cap 108 by positioning the wedge A 159, the wedge B 160, the wedge C 161 and the wedge D 162 of the lockout member 117, into the respective wedge guides A 173, B 174, C 175 and D 176, of the air sealing cap 108, respectively becoming 'clipped' in place, such that the lockout member 117 and the air sealing cap 108 cannot be easily decoupled.

Wedge guide A 173, wedge guide B 174, wedge guide C 175 and wedge guide D 176 are dimensioned to be wider (e.g., in a circumferential direction) than wedge A 159, wedge B 160, wedge C 161 and wedge D 162, such that rotational movement of the lockout member 117 about the axis A can still occur within the confines of the space defined by the wedge guides A 173, B 174, C 175 and D 176. Further coupling can occur between the lockout member 117 and the air sealing cap 108. For example, the outer ledge 146 and the guide 164 of the lockout member 117 can be received by the outer ledge recess 180 and the guide housing 181 of the air sealing cap 108.

The biasing element 182 in the guide housing 181 can be positioned to bias the lockout member 117 in the direction of the biasing force, i.e., to bias the lockout member 117 in its first direction (i.e., in the position in which the lockout member 117 locks the adapter 118 in its first position).

The canister 114 can be coupled to the actuator 109 by inserting the valve stem 116 of the canister 114 (see FIG. 3) into the stem socket 187 (see FIG. 13), passing through the center of lockout member 117 (see FIG. 3). The adapter 118 can be positioned over the canister 114 and at least the bottom section 132 of the adapter 118 can be received within the outer top cylinder 141 of the lockout member 117.

The lower cam linkage 120 can be slid onto the adapter 118, the arms 191 of the lower cam linkage being aligned to the flat portions 135 of the adapter 118 (see FIGS. 4, 7, 8 and 15). In this arrangement, the guides 137 of the adapter 118 are received by the guide recesses 192 of the lower cam linkage 120, limiting the adapter 118 and the lower cam linkage 120 to axial travel in the axial direction.

The arms 191 of the lower cam linkage 120 can be dimensioned to be received, and particularly, to pass through, the receiving slots 163 of the lockout member 117 (see FIG. 9) and further through the receiving slots 172 of the air sealing cap 108 (see FIG. 12). Rotation of the lockout member 117 is still permitted, as the width of the receiving slots 163 of the lockout member 117 is wider (i.e., in a circumferential direction with respect to the axial direction) than the width of the arms 191 of the lower cam linkage 120.

The axles 189 of the patient port cover 104 (see FIG. 14) can be dimensioned to be received in the cam axle receivers 178 of the arms 177 of the air sealing cap 108 (see FIG. 12). Furthermore, the cams 188 of the patient port cover 104 (see FIG. 14) can be dimensioned to be received in the cam guides 185 of the actuator 109 (see FIG. 13). In this position, the patient port cover 104 is coupled to, or in mechanical communication, with the lower cam linkage 120, e.g., the cams 188 are positioned to engage the arms 191 of the lower linkage cam 120 (see FIG. 6).

In some embodiments, the refill assembly 129 can be configured such that after the refill assembly 129 is assembled (as shown in FIG. 2), it cannot be disassembled, at least not without the use of destructive force and destruction to at least a portion of the refill assembly 129. For example, in some embodiments, the arms 191 of the lower cam linkage 120 can be splayed apart from one another to form an interference fit engagement that prevents the refill assembly 129 from being disassembled. As a result, in some embodiments, the canister 114 and the memory device 125 can remain together in the refill assembly 129.

Figure 16:
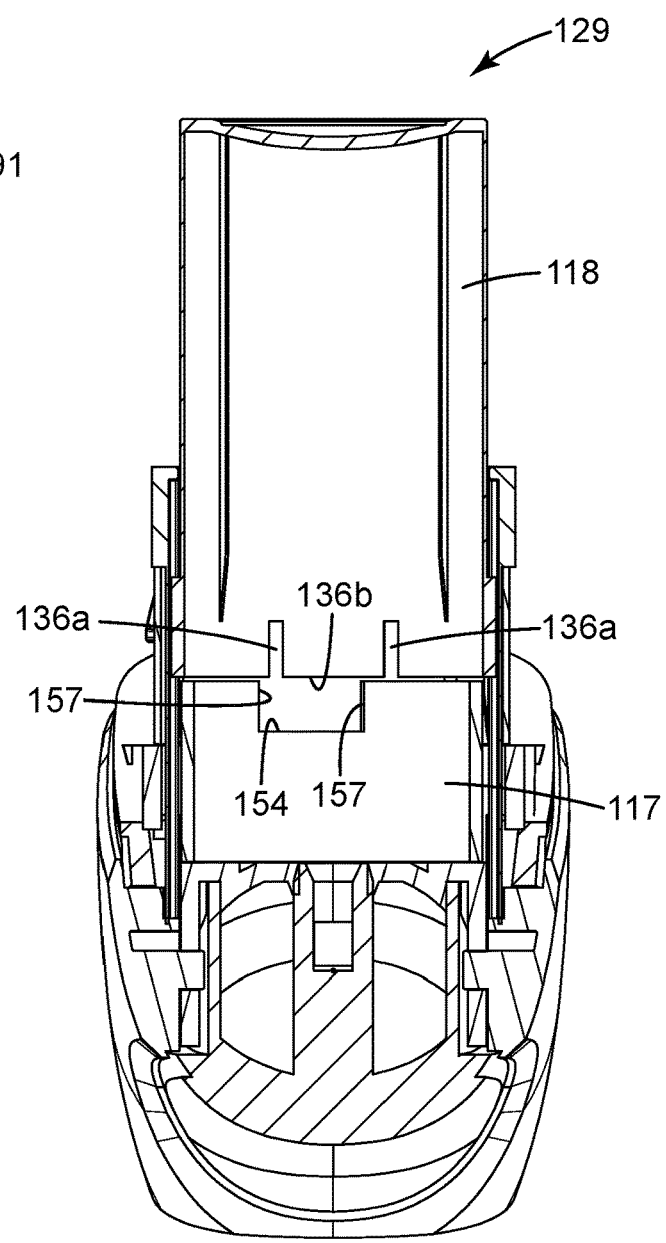
FIG. 16 is a rear cross-sectional view of the refill assembly of FIG. 2, with portions removed for clarity, and with the lockout member of FIGS. 9-11 shown in its first (locked) position.

FIG. 16 shows the refill assembly 129 (with the canister 114 absent for clarity), showing the lockout member 117 in its first (i.e., locked or lockout) position. The first position is achieved as force from the biasing element 182 acting on the guide 164 of the lockout member 117 causes the lockout member 117 to be rotated to a position where the ribs 157 of the lockout member 117 are not aligned, or able to engage, with the lockout recesses 136*a* of the adapter 118. This relative position of the adapter 118 with respect to the lockout member 117, and the respective first and second engagement features, physically prevents travel (e.g., axial travel) of the adapter 118 relative to the lockout member 117 when force is applied to the adapter 118 and/or the lockout member 117 (e.g., in the axial direction), such that the adapter 118 is locked in its first position, and a dose of medicament cannot be released (e.g., the canister 114 cannot be actuated).

Coupling the refill assembly 129 and a reusable assembly 128 of the present disclosure, however, results in sufficient rotation of the lockout member 117 to a precise position which brings about alignment of the first and second engagement features of the adapter 118 and the lockout member 117, respectively (i.e., alignment of the lockout recesses 136*a* and the projection 136*b* of the adapter 118 with the ribs 157 and the recess 154 or 155 of the lockout member 117, respectively). This is achieved by an interaction of the lockout member 117 with features of the reusable assembly 128, which will now be described. The second (i.e., unlocked) position of the lockout member 117, in which the adapter 118 is not locked in its first position, is illustrated in FIG. 23 and described in greater detail below.

Figure 17:
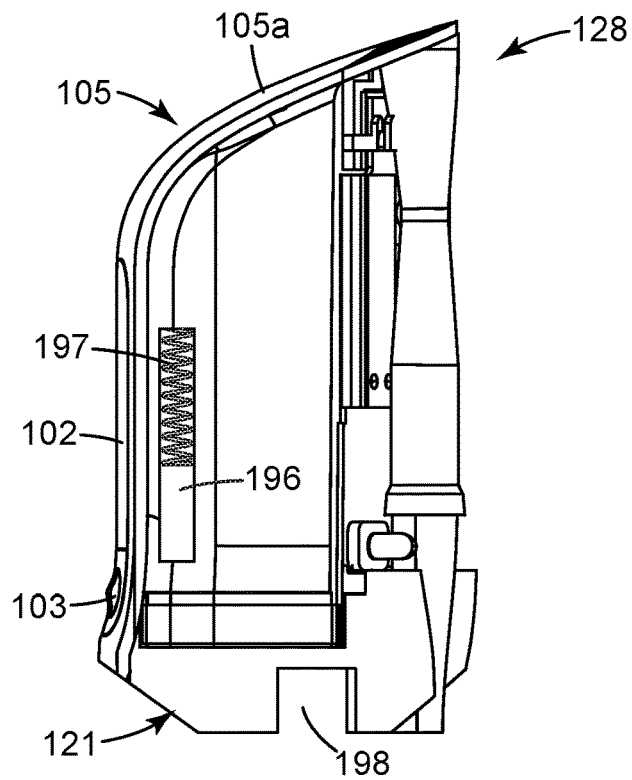
FIG. 17 is a side elevational view of the reusable assembly of FIG. 2, with the second portion of the outer housing removed to expose an inner housing.

FIG. 17 shows the reusable assembly 128 with the second portion 105*b* of the outer housing 105 removed for clarity. From FIG. 17 it can be seen that in some embodiments, the first portion 105*a* of the outer housing 105 can surround the display cover 102 and the control button 103 and can be coupled to the inner housing 121. As shown, the inner housing 121 can include features that interact with the second portion 105*b* of the outer housing 105 (which is referred to below as a "slide cover 105*b*" for simplicity) to limit the travel thereof. By way of example, the inner housing 121 can include one or more guides or channels 196—by way of example only, a pair of guides—with only one guide 196 being visible in FIG. 17. The one or more guides 196 can be dimensioned to receive a projection or other engagement feature of at least a portion of the outer housing 105, such as the slide cover 105*b*. In addition, a biasing element 197 can be positioned within each guide 196. By way of example only, the biasing element 197 is shown as being a coil spring, and particularly, a compression spring. As shown in FIG. 17, the inner housing 121 can further include one or more recesses or notches 198 dimensioned to receive a projection or other engagement feature of at least a portion of the outer housing 105, such as the slide cover 105*b*, to facilitate coupling and/or maintaining the outer housing 105 and the inner housing 121 together. The recesses 198 and guides 196 are shown by way of example only as being recessed in the inner housing 121 to receive a feature of the outer housing 105; however, it should be understood that alternatively the recesses 198 and/or the guides 196 could instead be projections dimensioned to be received in recesses or notches of the outer housing 105 and that the invention is not limited to the exemplary interengagement features shown in FIGS. 17-21.

Figure 18:
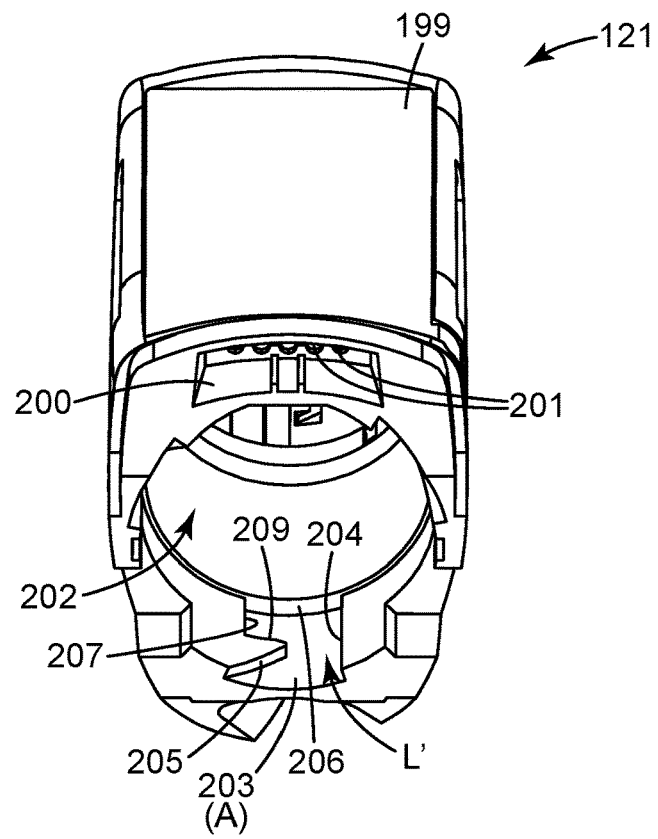
FIG. 18 is a bottom isometric view of the inner housing of the reusable assembly of FIG. 17.

The inner housing 121 of the present embodiment will now be described in further detail, with reference to FIGS. 18-20. As shown in FIG. 18, the inner housing 121 can include a display recess 199 dimensioned to receive the display 1001, a memory device housing recess 200 dimensioned to receive the memory device 125 and the memory device housing 166 (see FIG. 12), and five conduits 201 located above the memory device housing recess 200 that allow the memory device 125 of the refill assembly 129 to connect with the electronic interface 126, as shown in FIG. 3. As further shown in FIG. 18, the inner housing 121 can further include a chamber 202 that is dimensioned to receive at least a portion of the refill assembly 129, and particularly, at least a portion of one or more of the adapter 118, the lower cam linkage 120 and the canister 114 of the refill assembly 129, as shown in FIG. 3.

Additionally, as mentioned above, the reusable assembly 128 can include one or more second lockout engagement features L' that are configured to engage the first lockout engagement features L of the lockout member 117, and in some embodiments, the inner housing 121 can include one or more of these second lockout engagement features. For example, the inner housing 121 can include one or more sockets or recesses dimensioned to receive a post or tooth of the lockout member 117. By way of example, as shown in FIG. 18, the inner housing 121 can include a tooth socket A 203 located toward its bottom, having a side flat edge 204, a sloped edge (or angled wall) 205, a top edge 206, a short flat edge 207, and a ledge (or axial stop) 209 (e.g., a flat, e.g. horizontal, ledge), which are all positioned and configured to control or direct movement of the tooth A 147 of the lockout member 117 when the refill assembly 129 and the reusable assembly 128 are coupled together. For example, the sloped edge 205 is shaped to allow for axial and rotational movement between the tooth A 147 and the tooth socket A 203, and the flat ledge 209 is shaped to allow for relative rotational movement between the tooth A 147 and the tooth socket A 203. The edges 204, 205, 206 and 207 can instead be referred to as surfaces, walls, sections, portions, or the like.

Figure 19:
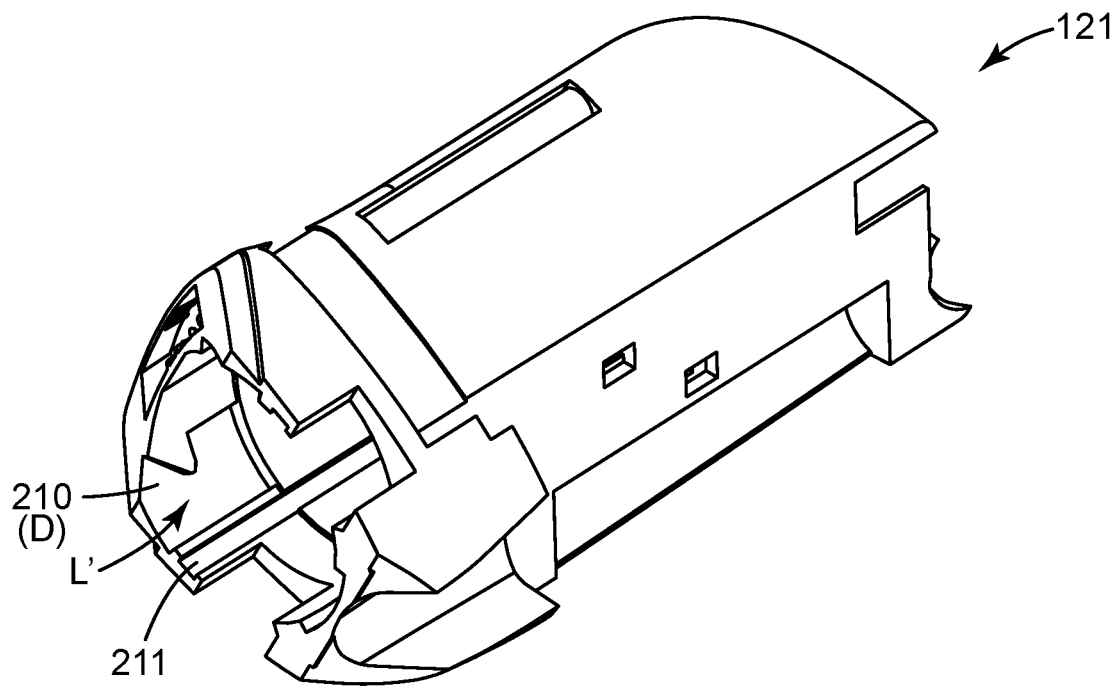
FIG. 19 is a side isometric view of the inner housing of FIG. 18.
Figure 20:
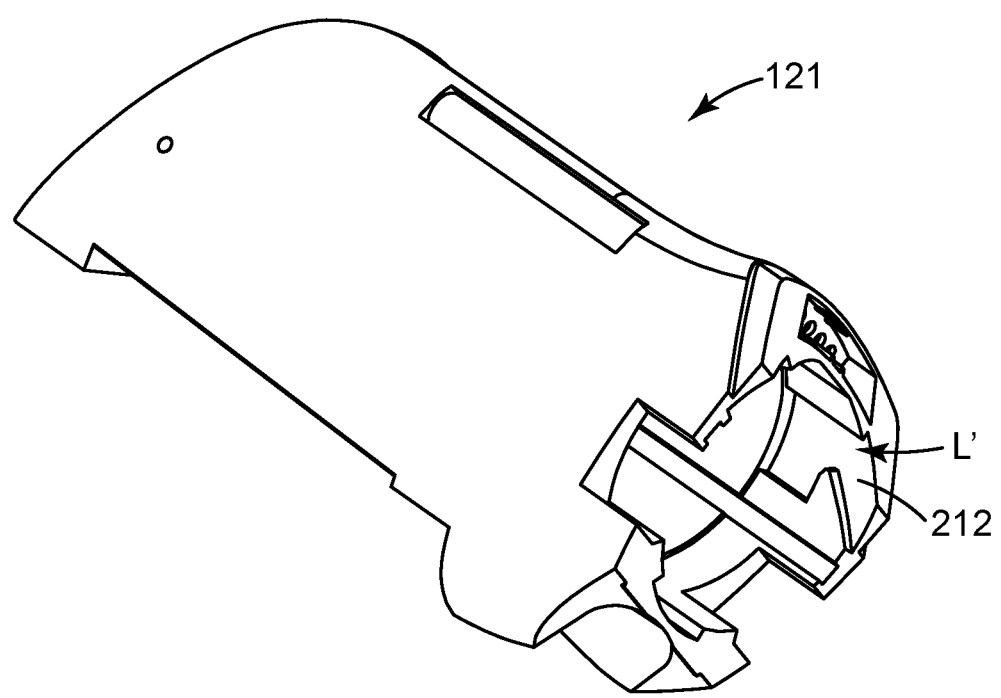
FIG. 20 is a side isometric view, opposite to that of FIG. 19, of the inner housing of FIGS. 18-19.

FIGS. 19 and 20 show the inner housing 121 from opposite sides. FIG. 19 shows that in some embodiments, the inner housing 121 can further include a tooth socket D 210 dimensioned to receive tooth D 150 of the lockout member 117 (see FIG. 10), and a guide 211. FIG. 20 shows that, in some embodiments, the inner housing 121 can further include a tooth socket C 212 dimensioned to receive tooth C 149 of the lockout member 117 (see FIG. 10). By way of example only, the tooth socket D 210 and the tooth socket C 212 are the same shape, size and have the same features (e.g., edges) as previously described for the tooth socket A 203.

Figure 21:
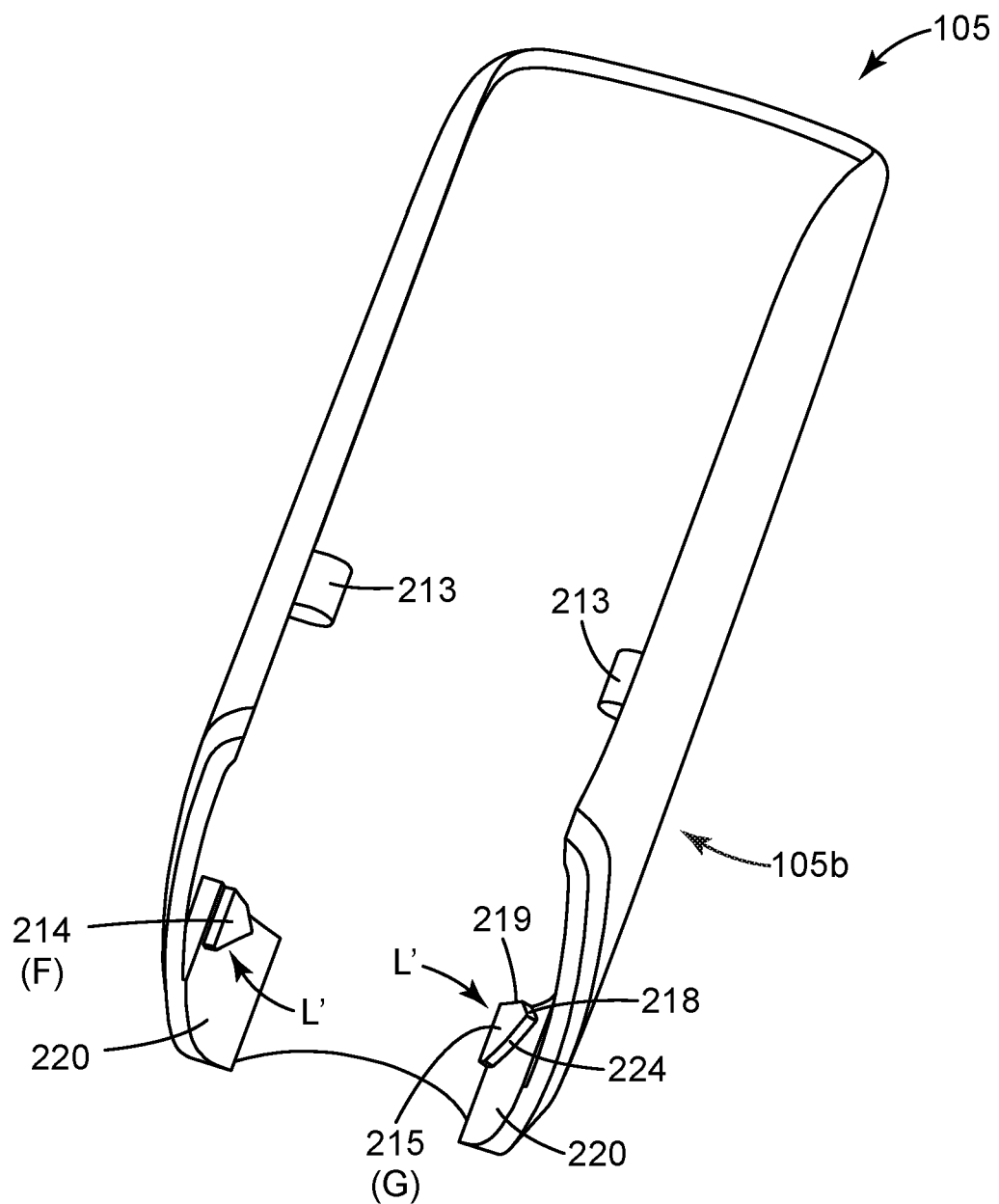
FIG. 21 is a front isometric view of the second portion of the outer housing of the reusable assembly of FIG. 2.

FIG. 21 illustrates the slide cover 105b of the inhaler 100, and particularly, of the reusable assembly 128 of the inhaler 100, which is configured to engage (e.g., to mate with) the inner housing 121 of the reusable assembly 128. As shown in FIG. 21, in some embodiments, the slide cover 105b can include one or more ribs (or pegs) 213 (e.g., on a front inner surface thereof). In addition, in some embodiments, the slide cover 105b can include one or more of the second lockout engagement features L', including a projection or tooth F 214 and a projection or tooth G 215, each dimensioned to be received in one of the recesses 198 of the inner housing 121 and configured to interact with one or more first lockout engagement features L of the lockout member 117 (as described below).

As shown in FIG. 21, the tooth G 215 includes a lower sloped edge 224, an upper sloped edge 218 and a top flat edge 219. The edges 224, 218 and 219 can instead be referred to as surfaces, walls, sections, portions, or the like. The tooth F 214 is shown by way of example as having the same outer profile as the tooth G 215. As further shown, the slide cover 105b can further include one or more projections 220 (e.g., in the form of a curved flat-topped projection) that each project radially inwardly from the inner surface of the slide cover 105b and axially upwardly from the bottom of the slide cover 105b, and that are each also positioned to connect a tooth (i.e., the tooth F 214 or the tooth G 215) to the inner surface of the slide cover 105b.

When the slide cover 105 is coupled to the inner housing 121, the ribs 213 (see FIG. 21) locate in the guides 196 of the inner housing 121 (see FIG. 17), with a biasing element 197 positioned above each rib 213 in the respective guide 196, providing a downward biasing force to the rib 213 in the guide 196. Furthermore, the projections 220 (see FIG. 21) are each positioned in a recess 198 of the inner housing 121 (see FIG. 17). This engagement between the projections 220 and the recesses 198, as well as that between the ribs 213 and the guides 196, ensures that when force is applied to the slide cover 105b, the slide cover is only permitted to travel axially but is limited and cannot be easily detached from the inner housing 121. In addition, the biasing elements 197, which become compressed when the slide cover 105 travels axially (e.g., axially upwardly), biasing the ribs 213 downwardly, ensure that the slide cover 105 returns to its original position when released by the patient.

When the refill assembly 129 is coupled to the reusable assembly 128, the first lockout engagement features L of the lockout member 117 engage with the second lockout engagement features L' of the reusable assembly 128 to cause the lockout member 117 to move from its first position to its second position and to inter-engagingly couple the refill assembly 129 and the reusable assembly 128 together. By way of example only, in the present embodiment, when the refill assembly 129 is coupled to the reusable assembly 128, the tooth A 147, tooth C 149 and tooth D 150 on the lockout member 117 (see FIGS. 9-11) engage with the tooth socket A 203, tooth socket C 212 and tooth socket D 210 of the inner housing 121 (see FIGS. 18-20), respectively. The interaction, i.e., engagement, of the tooth A 147 of the lockout member 117 and the tooth socket A 203 of the inner housing 121 will now be described in greater detail, with reference to FIGS. 22A-22D. It should be understood that in the present embodiment, the engagement of the tooth C 149 with the tooth socket C 212, as well as the engagement of the tooth D 150 with the tooth socket D 210 is identical to that of the tooth A 147 with the tooth socket A 203. As a result, reference is made to FIGS. 22A-22D and their accompanying description for these interactions as well.

FIGS. 22A-22D schematically illustrate the interaction of a first lockout engagement feature L (e.g., a post or a tooth) of the lockout member 117 of the refill assembly 129 with a second lockout engagement feature L' (e.g., a socket dimensioned to receive the post) of the reusable assembly 128 (e.g., of the inner housing 121 of FIGS. 18-20). More specifically for the present embodiment, FIGS. 22A-22D schematically illustrate the interaction of the tooth A 147 of the lockout member 117 (see FIGS. 9-11) with the tooth socket A 203 of the inner housing 121 (see FIG. 18).

As shown, the one or more first lockout engagement features L of the lockout member 117 and the second lockout engagement features L' of the reusable assembly 128 are movable relative to one another between a first position and a second position that correspond to the first position and the second position of the lockout member 117, respectively.

Figure 22A:
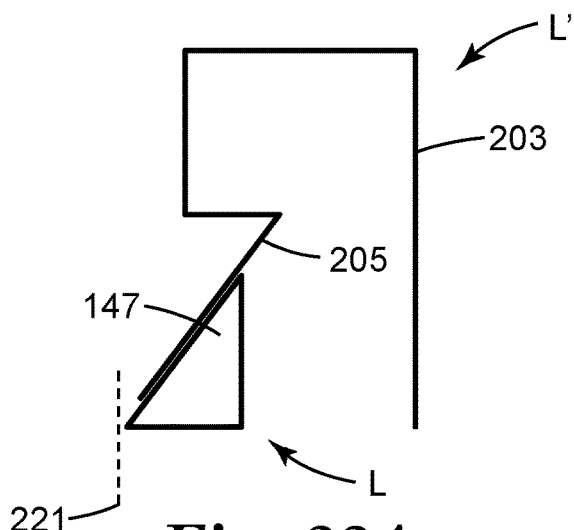
FIGS. 22A-22D schematically illustrate a process of unlocking the lockout member of FIGS. 9-11 of the refill assembly by coupling the refill assembly and the reusable assembly together, showing the interaction of a first lockout engagement feature of FIGS. 9-11 and a second lockout engagement feature of the reusable assembly of FIGS. 18-20.

FIG. 22A shows that the tooth A 147 abuts the sloped edge 205 of the tooth socket A 203 as the refill assembly 129 and the reusable assembly 128 are brought together (e.g., by moving the refill assembly 129 and the reusable assembly 128 axially together, in the axial direction). As shown in FIG. 22B, as additional force (e.g., in the axial direction) is applied to one or both of the refill assembly 129 and the reusable assembly 128 toward one another, the tooth A 147 moves further along, e.g., cams along, the sloped edge 205 of the tooth socket A 203. As the tooth A 147 is a feature of the lockout member 117 (see FIGS. 9 and 10), this movement of the tooth A 147 along the sloped edge 205 causes clockwise rotation of the lockout member 117 (e.g., about the axis A). This rotation also results in simultaneous movement of (i.e., rotation of) the guide 164 of the lockout member 117 (see FIG. 11) in the guide housing 181 of the air sealing cap 108, e.g., against the bias of the biasing element 182 (see FIG. 12), e.g., resulting in the biasing element 182 being compressed against its biasing force.

Figure 22C:
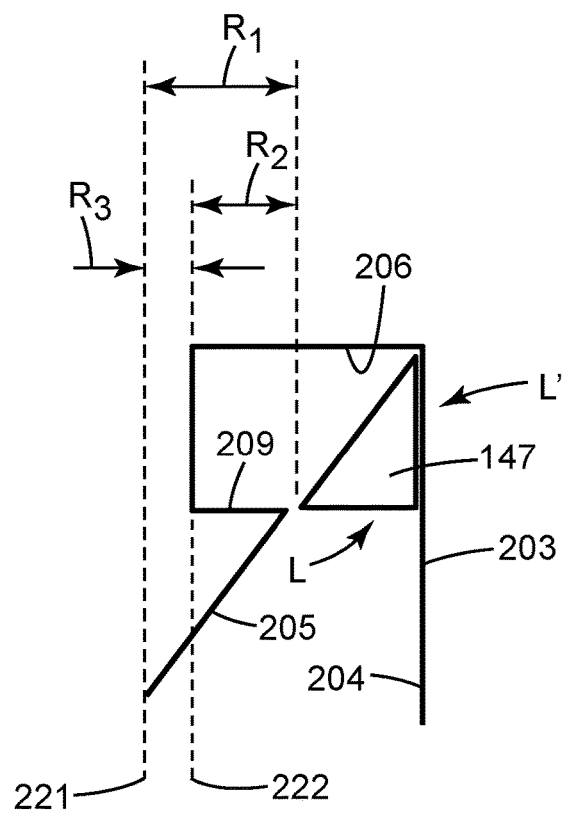
Figure 22B:
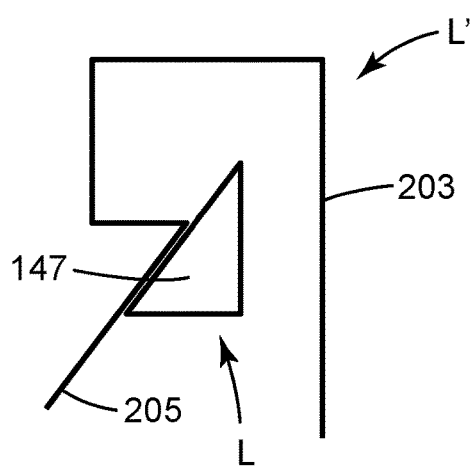

Clockwise rotation of the lockout member 117 ceases when the tooth A 147 disengages with the sloped edge 205 and engages with the side flat edge 204 and the top edge 206 of the tooth socket A 203, as shown in FIG. 22C. At this point, the biasing element 182 of in the guide housing 181 of the air sealing cap 108 is able to decompress, and the resultant force acts on the guide 164 of the lockout member 117, resulting in counter-clockwise rotation of the lockout member 117. The counter-clockwise rotation of the lockout member 117 results in horizontal movement (e.g., circumferential movement illustrated as linearly horizontal for simplicity in FIGS. 22C-22D) of the tooth A 147 in the tooth socket A 203, up to the point where the tooth A 147 contacts the short flat edge 207 of the tooth socket A 203 and rests atop the ledge 209, as shown in FIG. 22D.

Figure 22D:
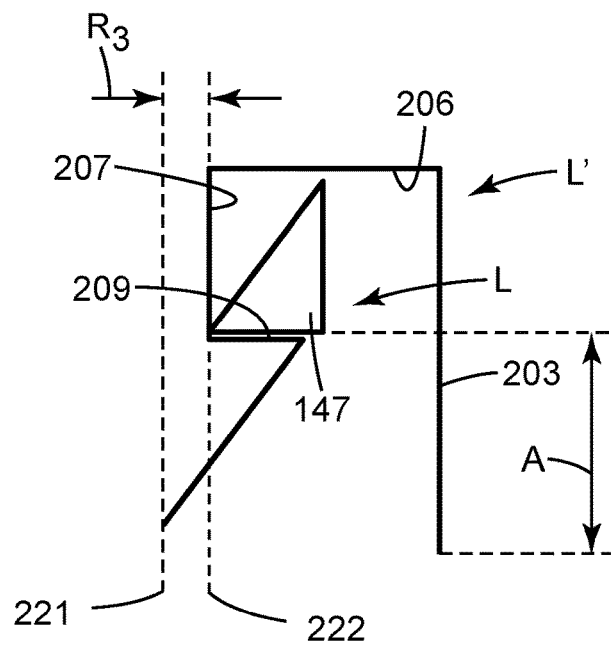

However, the starting position (e.g., starting circumferential or rotational position) 221 (see FIGS. 22A, 22C and 22D) of the tooth A 147 is not aligned with its end position (e.g., end circumferential or rotational position) 222 (see FIGS. 22C and 22D). As a result, the lockout member 117 does not return to its starting position (e.g., its starting rotational position about the axis A), but instead it comes to rest at a rotational position at which it is unlocked. That is, in some embodiments, the first and second positions of the lockout member 117 (e.g., with respect to the reusable assembly 128), as shown in FIGS. 22A and 22D, can be displaced relative to one another, the displacement having both an axial component and a rotational or circumferential component, such that the lockout member 117 can have a first axial position, a first rotational position, a second axial position and a second rotational position. The first rotational position 221 is shown in FIGS. 22A, 22C and 22D, and the second rotational position 222 is shown in FIGS. 22C and 22D.

As the refill assembly 129 is coupled to the reusable assembly 128, the lockout member 117 of the present embodiment moves axially to a second axial position that is axially spaced from the first axial position, and further moves rotationally to a second rotational position that is rotationally (or circumferentially) spaced from the first rotational position. Furthermore, the second lockout engagement features L' of the reusable assembly 128 are configured such that the lockout member 117 is biased in its second position once the second position is achieved (e.g., at least partially due to the bias of the biasing element 182 in the guide housing 181 of the air sealing cap 108). As a result, the first lockout engagement feature(s) L and the second lockout engagement feature(s) L' are configured to remain in the second position relative to one another when the refill assembly 129 is coupled to a reusable assembly 128. The first and second positions shown in FIGS. 22A and 22D, respectively, can also be referred to as first and second positions of the first lockout engagement feature L and the second lockout engagement feature L', relative to one another.

In some embodiments, the intermediate position of the tooth A 147 in the tooth socket A 203 shown in FIG. 22C can be referred to as a third position of the first and second lockout engagement features L, L' and/or of the lockout member 117. In some embodiments, as shown, the third position can be located between, or intermediate of, the first position and the second position. Particularly, the first position and the third position can be separated by an axial distance A (see FIG. 22D) and a first rotational distance $R_1$ (see FIG. 22C); the third position and the second position can be separated by a second rotational distance $R_2$ (see FIG. 22C), i.e., while not being separated axially; and the first position and the second position can be separated by the same axial distance A (see FIG. 22D) and a third rotational distance $R_3$ (see FIGS. 22C and 22D) that is less than the first rotational distance $R_1$ (i.e., the first and second positions are spaced apart axially and rotationally). In the present embodiment, as shown in FIG. 22C, the third rotational distance $R_3$ is equal to the difference between the first rotational distance $R_1$ and the second rotational distance $R_2$. The third rotational distance $R_3$ corresponds to the rotational component of the displacement between the first and second positions of the lockout member 117.

In the second position of the lockout member 117 and of the first and second lockout engagement features L, L', the second engagement features of the lockout member 117 (e.g., the ribs 157 and the recesses 154, 155) are aligned, or able to engage, with the first engagement features of the adapter 118 (e.g., the lockout recesses 136a and the projection 136b of the adapter 118), as shown in FIG. 23. That is, FIG. 23 shows the inhaler 100 with the refill assembly 129 (with the canister 114 absent for clarity) and the reusable assembly 128, showing the lockout member 117 in its second (i.e., unlocked) position, wherein the adapter 118 is free to move from its first position to its second position, and is also free to move from its second position back to its first position (i.e., between its first and second positions). Particularly, as shown in FIG. 23, when the lockout member 117 is in its second position, the respective first and second engagement features of the lockout member 117 and the adapter 118 are aligned, such that travel (e.g., axial travel) of the adapter 118 relative to the lockout member 117 is possible when force is applied to the adapter 118 and/or the lockout member 117 (e.g., in the axial direction), such that the adapter 118 can be moved to its second position and a dose of medicament can be released (e.g., the canister 114 can be actuated).

As a result, in the present embodiment, due to the axially oriented nature of the respective engagement features of the adapter 118 and the lockout member 117, the first engagement features of the adapter 118 and the second engagement features of the lockout member 117 are movable into and out of engagement in response to relative movement of the adapter 118 and the lockout member 117 in the axial direction (e.g., along the axis A).

During the process of coupling of the refill assembly 129 and the reusable assembly 128, the tooth B 148 and the tooth E 151 of lockout member 117 (see FIG. 11) are positioned and configured to interact with the tooth G 215 and the tooth F 214, respectively, of the slide cover 105b (see FIG. 21). As the coupling occurs, the sloped top edges 152 of the teeth B 148 and E 151 come into contact with the lower sloped edges 224 of the teeth G 215 and F 214 respectively. The clockwise rotation of the lockout member 117 caused by the interaction of the first and second lockout engagement features L, L', which occurs as the refill assembly 129 and the reusable assembly 128 are pushed together, causes the sloped top edges 152 of the teeth B 148 and E 151 to cam along the lower sloped edges 224 of the teeth G 215 and F 214 respectively. Upon full clockwise travel, the sloped top edges 152 of the teeth B 148 and E 151 disengage from the lower sloped edges 224 of the teeth G 215 and F 214. The immediately subsequent counter-clockwise rotation of the lockout member 117, under the influence of the biasing element 182, causes the upper sloped edge 218 of each of the tooth G 215 and the tooth F 214 to engage with the sloped bottom edge 153 of the tooth B 148 and the tooth E 151, respectively.

Additionally, interaction of the tooth A 147, the tooth C 149 and the tooth D 150 with the tooth socket A 203, the tooth socket C 212 and the tooth socket D 210, respectively, serves to secure the refill assembly 129 and reusable assembly 128 to prevent unintentional separation of the two parts during usage, e.g. during shaking (e.g., at least partly because of the tooth being inhibited against axial movement by the respective ledge 209 of the tooth socket).

In order to remove the refill assembly 129, i.e., to decouple the refill assembly 129 and the reusable assembly 128, the patient can place a hand on the slide cover 105b of the reusable assembly 128 and grip the refill assembly 129 (e.g., by the actuator 109 and/or the patient port cover 104) with the other hand. When a pulling force is applied to the refill assembly 129, the slide cover 105b moves upwards, due to the interaction of the ribs 213 of the slide cover 105b (see FIG. 21) with the biasing elements 197 in the guides 196 of the inner housing 121 (See FIG. 17), thereby compressing the biasing elements 197. This action causes the lockout member 117 to start to move from its second position. By way of example, in the present embodiment, the above action causes clockwise rotation of the lockout member 117 due to the cam action brought by the interaction of the tooth E 151 and the tooth B 148 of lockout member 117 with the tooth F 214 and the tooth G 215 of the slide cover 105b, respectively. The clockwise rotation of the lockout member 117 causes the tooth A 147, the tooth C 149, and the tooth D 150 to disengage from the tooth socket A 203, the tooth socket C 212 and the tooth socket D 210 (e.g., by moving out of engagement with the ledge 209—see FIG. 22C) in a reverse sequence to that shown in FIGS. 22A-22D, namely, to move the first and second lockout engagement features L, L' from the second position (see FIG. 22D) to the third position (see FIG. 22C) and back to the first position (see FIG. 22A).

When the refill assembly 129 is removed from the reusable assembly 128, the lockout member 117 therefore returns to its first position with respect to the adapter 118, where the ribs 157 and the recesses 154, 155 of the lockout member 117 are no longer aligned, or able to engage, with the lockout recesses 136a and the projection 136b, respectively, of the adapter 118, thus preventing the canister 114 from being actuated. The slide cover 105b is returned to its original position by the force resulting from the decompression of the biasing elements 197 in the guides 196 of the inner housing 121 acting on the ribs 213 of the slide cover 105b.

As described above, the removal of the refill assembly 129 from the reusable assembly 128 is achieved by travel (e.g., axial travel in the axial direction) of the slide cover 105b, which causes clockwise rotation of the lockout member 117 due to the cam action brought by the interaction of the tooth E 151 and the tooth B 148 of the lockout member 117 with the tooth F 214 and the tooth G 215 of the slide cover 105b, respectively. In a further embodiment, the same outcome can be achieved without the use of the slide cover 105b, as will now be described.

Figure 24:
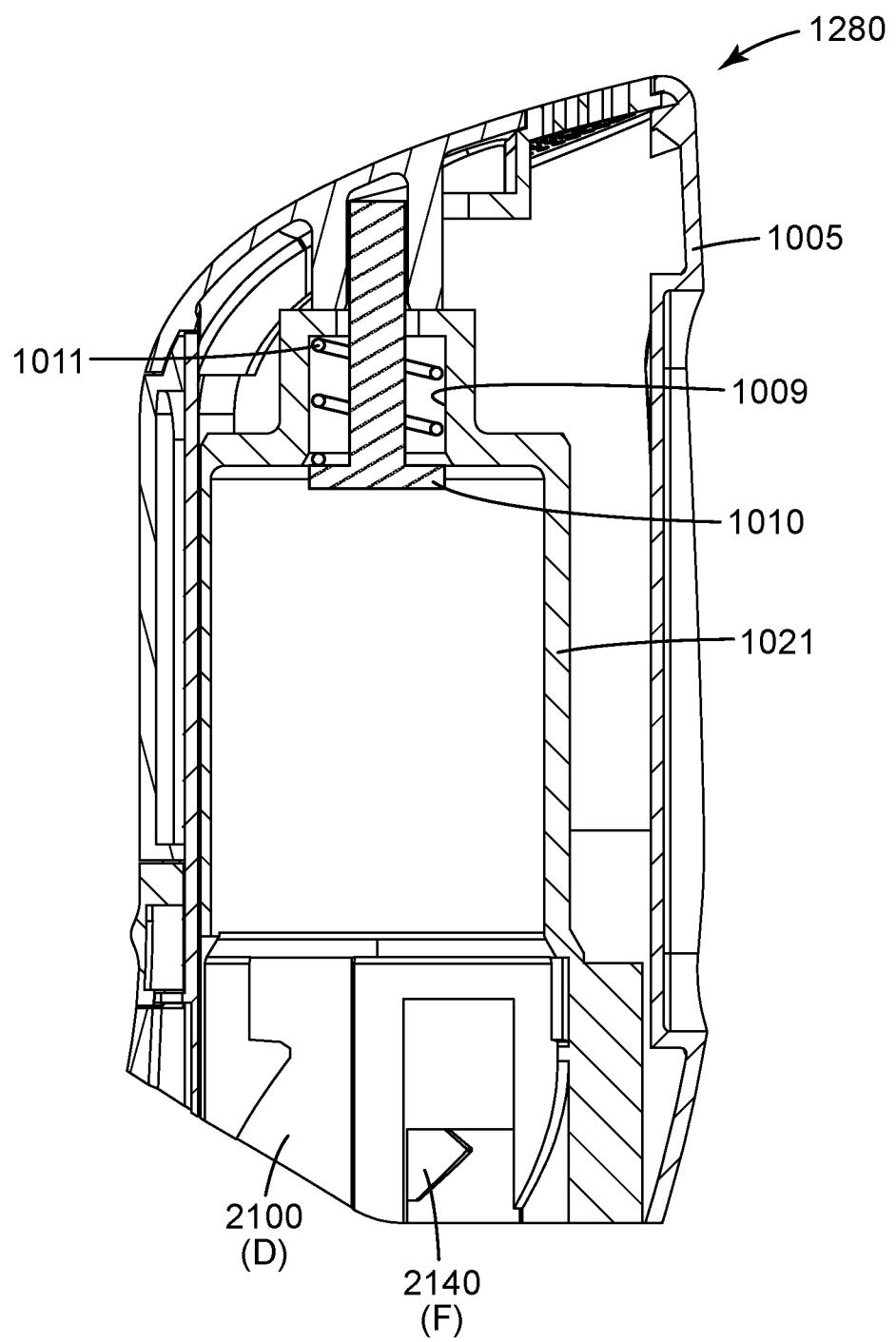
FIG. 24 is a side cross-sectional view of a housing of a reusable assembly according to another embodiment of the present disclosure.
Figure 25:
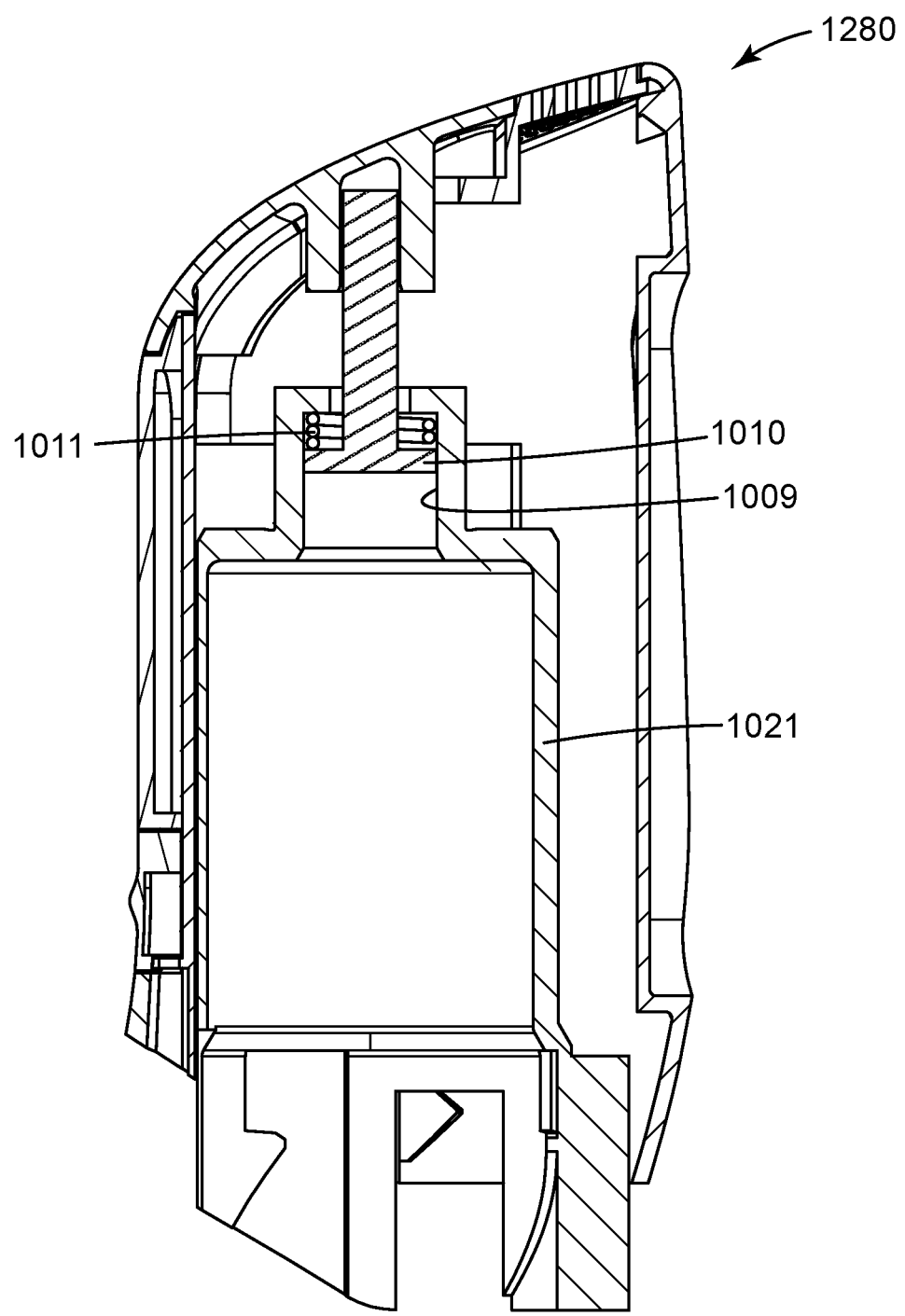
FIG. 25 is a side cross-sectional view of the reusable assembly housing of FIG. 24, shown immediately after decoupling the reusable assembly from a refill assembly.

FIGS. 24 and 25 illustrate a reusable assembly housing 1280 according to another embodiment of the present disclosure that can be employed in, or form a portion of, reusable assemblies and inhalers of the present disclosure. The housing 1280 of FIGS. 24-25 shares many of the same elements, features, and functions as the outer housing 105 and inner housing 121 described above with respect to the embodiment of FIGS. 1-23. Reference is made to the description above accompanying FIGS. 1-23 for a more complete description of the features and elements (and alternatives to such features and elements) of the embodiment illustrated in FIGS. 24-25. Any of the features described above with respect to FIGS. 1-23 can be applied to the embodiment of FIGS. 24-25, and vice versa.

FIG. 24 shows a portion of a reusable assembly housing 1280, comprising an outer housing 1005, and a moveable inner housing 1021, that can be coupled to the outer housing 1005 by a variety of coupling means. Such coupling means can include, but are not limited to, press-fit or friction-fit engagement, snap-fit engagement, magnets, hook-and-loop fasteners, adhesives, cohesives, clamps, heat sealing, stitches, staples, screws, nails, rivets, brads, bolts, crimps, welding (e.g., sonic (e.g., ultrasonic) welding), any thermal bonding technique (e.g., heat and/or pressure applied to one or both of the components to be coupled), other suitable coupling means, or combinations thereof. By way of example only, FIGS. 24 and 25 show the inner housing 1021 being coupled to the outer housing 1005 by a bolt 1010. As further shown in FIGS. 24 and 25, the housing 1280 can further include a biasing element 1011 (e.g., a spring), which is shown as a coil spring, and particularly, a compression spring, by way of example only. The biasing element 1011 is positioned within a chamber 1009 dimensioned to receive the bolt, the biasing element 1011 shown as being located in the chamber 1009 between the bolt 1010 and an inner surface of the chamber 1009.

As shown in FIG. 24, the outer housing 1005 can further include a tooth F 2140. A further tooth exists, a tooth G, located on the opposite side of the housing 1280, but it is not visible in FIG. 24 or FIG. 25. The teeth F 2140 and G (not shown) of the housing 1280 are identical in form and function to the teeth F 214 and G 215, respectively, of the slide cover 105b, as described with respect to FIG. 21.

As shown in FIG. 24, the inner housing 1021 further includes a tooth socket D 2100. Two further sockets exist (i.e., a tooth socket A and a tooth socket C) but are not visible in FIG. 24 or FIG. 25. The tooth sockets D 2100 and A and C (not shown) are identical in form and function to the tooth socket D 210 (see FIG. 19), the tooth socket A 203 (see FIG. 18) and the tooth socket C 212 (see FIG. 20), as described above with respect to FIGS. 18-20.

To remove the refill assembly 129 from a reusable assembly comprising the housing 1280, a patient grips the housing 1280 and pulls on the refill assembly 129. This causes the inner housing 1021 to travel axially and the biasing element 1011 to become compressed, as shown in FIG. 25. This movement causes clockwise rotation of the lockout member 117 due to the cam action brought by the interaction of the tooth E 151 and tooth B 148 of the lockout member 117 with the tooth F 2140 and the tooth G (not shown), of the outer housing 1005, respectively.

The clockwise rotation of the lockout member 117 causes the tooth A 147, the tooth C 149, and the tooth D 150 to disengage from the tooth socket A (not shown), the tooth socket C (not shown) and the tooth socket D 2100 (see FIG. 24), e.g., by moving out of engagement with the ledge 209 (see FIG. 22C) in a reverse sequence to that shown in FIGS. 22A-22D, namely, to move the first and second lockout engagement features L, L' from the second position (see FIG. 22D) to the third position (see FIG. 22C) and back to the first position (see FIG. 22A).

When the refill assembly 129 is removed from the reusable assembly comprising the housing 1280, the lockout member 117 returns to its first position with respect to the adapter 118, where the ribs 157 and the recesses 154, 155 of the lockout member 117 are no longer aligned with the lockout recesses 136a and the projection 136b, respectively, of the adapter 118, thus preventing the canister 114 from being actuated. Once the refill assembly 129 is removed from the reusable assembly 1280, the biasing element 1011 decompresses and forces the inner housing 1021 to return to its original position, as shown in FIG. 24.

Each embodiment shown in the figures is illustrated as a separate embodiment for clarity in illustrating a variety of features of the inhalers, or portions thereof, of the present disclosure. However, it should be understood that any combination of elements and features of any of the embodiments illustrated in the figures and described herein can be employed in the inhalers, the refill assemblies and/or the reusable assemblies of the present disclosure.

The following embodiments are intended to be illustrative of the present disclosure and not limiting.

Embodiments

1. A refill assembly for use in a medicinal inhaler and configured to be removably coupled to a reusable assembly of a medicinal inhaler, the refill assembly comprising:
   a patient port;
   an adapter configured to cause a dose of medicament to be released, the adapter movable between a first position in which a dose of medicament is not released and a second position in which a dose of medicament is released; and
   a lockout member movable between (i) a first position in which the adapter is not movable from its first position to its second position, and (ii) a second position in which the adapter is movable from its first position to its second position;
   wherein the lockout member is in its first position when the refill assembly is not coupled to a reusable assembly and is in its second position when the refill assembly is coupled to a reusable assembly.

2. The refill assembly of embodiment 1, wherein when the lockout member is in the second position, the adapter is movable between its first position and its second position.

3. The refill assembly of embodiment 1 or 2, wherein when the lockout member is in the second position, the adapter is further movable from its second position to its first position.

4. The refill assembly of any of embodiments 1-3, further comprising an axis that defines an axial direction that extends along or substantially parallel to the axis, and wherein the adapter is movable in the axial direction between its first position and its second position.

5. The refill assembly of any of embodiments 1-4, further comprising an axis that defines an axial direction that extends along or substantially parallel to the axis, and wherein the adapter and the lockout member are movable in the axial direction relative to one another when the lockout member is in its second position.

6. The refill assembly of any of embodiments 1-5, wherein the lockout member is rotatable between its first position and its second position.

7. The refill assembly of any of embodiments 1-6, further comprising an axis, and wherein the lockout member is rotatable between its first position and its second position about the axis.

8. The refill assembly of any of embodiments 1-7, wherein the reusable assembly includes a dose release firing system configured to cause the adapter to move from its first position to its second position.

9. The refill assembly of any of embodiments 1-8, wherein the adapter is configured to receive at least a portion of a canister, the canister comprising a medicament and a dose release valve, the adapter movable between a first position in which the dose release valve is not actuated to release a dose of medicament and a second position in which the dose release valve is actuated to release a dose of medicament.

10. The refill assembly of any of embodiments 1-9, further comprising a memory device configured to be operatively coupled to a controller in the reusable assembly when the refill assembly and the reusable assembly are coupled together.

11. The refill assembly of any of embodiments 1-10, wherein the lockout member includes a lockout collar configured to receive at least a portion of the adapter.

12. The refill assembly of any of embodiments 1-11, wherein the lockout member is biased in its first position.

13. The refill assembly of any of embodiments 1-12, wherein the lockout member is movable from its first position to its second position in response to the refill assembly and the reusable assembly being coupled together.

14. The refill assembly of any of embodiments 1-13, wherein the adapter includes a first engagement feature and the lockout member includes a second engagement feature configured to engage the first engagement feature, and wherein the first engagement feature and the second engagement feature are not aligned or able to engage when the lockout member is in the first position, and wherein the first engagement feature and the second engagement feature are aligned and able to engage when the lockout member is in the second position.

15. The refill assembly of embodiment 14, further comprising an axis that defines an axial direction that extends along or substantially parallel to the axis, and wherein the first engagement feature and the second engagement feature are movable into and out of engagement in response to relative movement of the adapter and the lockout member in the axial direction.

16. The refill assembly of any of embodiments 1-15, wherein the lockout member includes a first lockout engagement feature configured to engage a second lockout engagement feature of a reusable assembly, wherein the first lockout engagement feature and the second lockout engagement feature are movable relative to one another between a first position and a second position that correspond to the first position and the second position of the lockout member, respectively.

17. The refill assembly of embodiment 16, wherein the first lockout engagement feature and the second lockout engagement feature are configured to retain the second position relative to one another when the refill assembly is coupled to a reusable assembly.

18. The refill assembly of embodiment 16 or 17, wherein the first position and the second position of the first lockout engagement feature and the second lockout engagement feature are spaced apart axially and rotationally.

19. The refill assembly of any of embodiments 16-18, wherein the first lockout engagement feature and the second lockout engagement feature are further movable to a third position relative to one another, between the first position and the second position, wherein the first position and the third position are separated by an axial distance and a first rotational distance, wherein the third position and the second position are separated by a second rotational distance, and wherein the first position and the second position are separated by the axial distance and a third rotational distance that is less than the first rotational distance.

20. The refill assembly of embodiment 19, wherein the third rotational distance is equal to the difference between the first rotational distance and the second rotational distance.

21. The refill assembly of any of embodiments 1-20, wherein the reusable assembly or the lockout member includes a socket dimensioned to receive a post of the lockout member or the reusable assembly, respectively, wherein the socket and the post are movable relative to one another between a first position and a second position that correspond to the first position and the second position of the lockout member, respectively.

22. The refill assembly of embodiment 21, wherein the socket and the post are configured to be maintained in the second position when the refill assembly is coupled to the reusable assembly.

23. The refill assembly of embodiment 21 or 22, further comprising an axis that defines an axial direction that extends along or substantially parallel to the axis, wherein the refill assembly and the reusable assembly are configured to be coupled together by moving the refill assembly and the reusable assembly toward one another in the axial direction, and wherein the first position and the second position of the post and the socket are spaced apart axially and rotationally.

24. The refill assembly of any of embodiments 21-23, wherein the socket includes an angled wall that allows for relative axial and rotational movement between the post and the socket and a ledge that allows for relative rotational movement between the post and the socket at a given axial position.

25. The refill assembly of any of embodiments 21-24, wherein the post includes a triangular-shaped member.

26. The refill assembly of any of embodiments 1-25, further comprising a housing, wherein the patient port is formed in a portion of the housing dimensioned to receive and be coupled to at least a portion of the lockout member.

27. The refill assembly of any of embodiments 1-26, wherein the lockout member is dimensioned to receive at least a portion of the adapter.

28. The refill assembly of any of embodiments 1-27, further comprising a refill air flow path comprising an air inlet and an air outlet, and wherein the patient port defines the air outlet.

29. An inhaler comprising:
the refill assembly of embodiment 1; and
a reusable assembly configured to be coupled to the refill assembly, the reusable assembly comprising a dose release firing system configured to cause the adapter to move from its first position to its second position.

30. The inhaler of embodiment 29, wherein the refill assembly is releasable from the reusable assembly after it has been coupled to the reusable assembly.

31. The inhaler of embodiment 29 or 30, wherein the refill assembly and the reusable assembly are configured to be coupled together and further decoupled from one another.

32. The inhaler of any of embodiments 29-31, wherein the dose release firing system is breath-actuated.

33. The inhaler of any of embodiments 29-32, further comprising an axis that defines an axial direction that extends along or substantially parallel to the axis, wherein the refill assembly and the reusable assembly are configured to be coupled together by moving the refill assembly and the reusable assembly toward one another in the axial direction.

34. The inhaler of any of embodiments 29-33, wherein the dose release firing system includes a stored energy device configured to drive the adapter from the first position to the second position when stored energy in the stored energy device is released, wherein the firing system is in a primed state when the stored energy is not released, and wherein the firing system is in a fired state when the stored energy is released.

35. The inhaler of any of embodiments 29-34, wherein the reusable assembly further includes means for moving the lockout member to its second position in response to the refill assembly and the reusable assembly being coupled together.

36. The inhaler of any of embodiments 29-35, wherein the reusable assembly further includes a flow governor for governing airflow through the inhaler.

37. The inhaler of any of embodiments 29-36, wherein the reusable assembly further includes a flow governor assembly comprising a flow governor and at least one pressure sensor positioned in fluid communication with the flow governor.

38. The inhaler of any of embodiments 29-37, wherein the reusable assembly further includes a controller, and a power source.

39. The inhaler of any of embodiments 29-38, wherein the reusable assembly further includes a display.

40. The inhaler of any of embodiments 29-39, wherein the reusable assembly further includes at least one pressure sensor.

41. The inhaler of any of embodiments 29-40, wherein the refill assembly includes a refill air flow path comprising an air inlet and an air outlet, and wherein the patient port defines the air outlet.

42. The inhaler of any of embodiments 29-41, wherein the reusable assembly includes a reusable air flow path comprising an air inlet and an air outlet, and wherein the reusable assembly and the refill assembly are configured to be coupled together to fluidly couple the air outlet of the reusable air flow path and an air inlet of the refill assembly.

43. The inhaler of any of embodiments 29-42, wherein at least one of the reusable assembly and the refill assembly includes a display.

44. The inhaler of any of embodiments 29-43, further comprising an axis that defines an axial direction that extends along or substantially parallel to the axis, and wherein the adapter is movable in the axial direction between its first position and its second position.

45. The inhaler of any of embodiments 29-44, further comprising an axis that defines an axial direction that extends along or substantially parallel to the axis, and wherein the adapter and the lockout member are movable in the axial direction relative to one another when the lockout member is in its second position.

46. The inhaler of any of embodiments 29-45, wherein the lockout member is rotatable between its first position and its second position.

47. The inhaler of any of embodiments 29-46, further comprising an axis, and wherein the lockout member is rotatable between its first position and its second position about the axis.

48. The inhaler of any of embodiments 29-47, wherein the reusable assembly includes a first lockout engagement feature and the lockout member includes a second lockout engagement feature configured to engage the first lockout engagement feature, wherein the first lockout engagement feature and the second lockout engagement feature are movable relative to one another between a first position and a second position that correspond to the first position and the second position of the lockout member, respectively.

49. The inhaler of embodiment 48, wherein the first lockout engagement feature and the second lockout engagement feature are configured to be maintained in the second position when the refill assembly is coupled to the reusable assembly.

50. The inhaler of any of embodiments 29-49, wherein the reusable assembly or the lockout member includes a socket dimensioned to receive a post of the lockout member or the reusable assembly, respectively, wherein the socket and the post are movable relative to one another between a first position and a second position that correspond to the first position and the second position of the lockout member, respectively.

51. The inhaler of embodiment 50, wherein the socket and the post are configured to be maintained in the second position when the refill assembly is coupled to the reusable assembly.

52. The inhaler of embodiment 50 or 51, further comprising an axis that defines an axial direction that extends along or substantially parallel to the axis, wherein the refill assembly and the reusable assembly are configured to be coupled together by moving the refill assembly and the reusable assembly toward one another in the axial direction, and wherein the first position and the second position of the post and the socket are spaced apart axially and rotationally.

53. The inhaler of embodiment 52, wherein the socket includes an angled wall that allows for relative axial and rotational movement between the post and the socket and a ledge that allows for relative rotational movement between the post and the socket at a given axial position.

54. The inhaler of any of embodiments 50-53, wherein the post includes a triangular-shaped member.

It is to be understood that the invention is not limited in its application to the details of construction and the arrangement of components set forth in the above description or illustrated in the accompanying drawings. The invention is capable of other embodiments and of being practiced or of being carried out in various ways. Also, it is to be understood that the phraseology and terminology used herein is for the purpose of description and should not be regarded as limiting. It is to be further understood that other embodiments may be utilized, and structural or logical changes may be made without departing from the scope of the present disclosure.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A refill assembly for use in a medicinal inhaler and configured to be removably coupled to a reusable assembly of the medicinal inhaler, the refill assembly comprising:

a patient port;
an adapter configured to cause a dose of medicament to be released, the adapter movable between a first position in which a dose of medicament is not released and a second position in which the dose of medicament is released; and
a lockout member rotatable between (i) a first position in which the adapter is not movable from its first position to its second position, and (ii) a second position in which the adapter is movable from its first position to its second position;
wherein the lockout member is in its first position when the refill assembly is not coupled to the reusable assembly and is in its second position when the refill assembly is coupled to the reusable assembly; and
wherein the adapter is configured to receive at least a portion of a canister, the canister comprising a medicament and a dose release valve, the adapter movable between the first position in which the dose release valve is not actuated to release a dose of medicament and the second position in which the dose release valve is actuated to release a dose of medicament.

2. The refill assembly of claim 1, wherein when the lockout member is in its second position, the adapter is further movable from its second position to its first position.

3. The refill assembly of claim 1, further comprising an axis that defines an axial direction that extends along or substantially parallel to the axis, and wherein the adapter is movable in the axial direction between its first position and its second position.

4. The refill assembly of claim 1, further comprising an axis that defines an axial direction that extends along or substantially parallel to the axis, and wherein the adapter and the lockout member are movable in the axial direction relative to one another when the lockout member is in its second position.

5. The refill assembly of claim 1, wherein the reusable assembly includes a dose release firing system configured to cause the adapter to move from its first position to its second position.

6. The refill assembly of claim 1, further comprising a memory device configured to be operatively coupled to a controller in the reusable assembly when the refill assembly and the reusable assembly are coupled together.

7. The refill assembly of claim 1, wherein the lockout member is movable from its first position to its second position in response to the refill assembly and the reusable assembly being coupled together.

8. The refill assembly of claim 1, wherein the adapter includes a first engagement feature and the lockout member includes a second engagement feature configured to engage the first engagement feature, and wherein the first engagement feature and the second engagement feature are not aligned or able to engage when the lockout member is in the first position, and wherein the first engagement feature and the second engagement feature are aligned and able to engage when the lockout member is in the second position.

9. The refill assembly of claim 1, wherein the lockout member includes a first lockout engagement feature configured to engage a second lockout engagement feature of a reusable assembly, wherein the first lockout engagement feature and the second lockout engagement feature are movable relative to one another between a first position and a second position that correspond to the first position and the second position of the lockout member, respectively.

10. The refill assembly of claim 1, wherein the reusable assembly or the lockout member includes a socket dimensioned to receive a post of the lockout member or the reusable assembly, respectively, wherein the socket and the post are movable relative to one another between a first position and a second position that correspond to the first position and the second position of the lockout member, respectively.

11. An inhaler comprising:
   the refill assembly of claim 1; and
   a reusable assembly configured to be coupled to the refill assembly, the reusable assembly comprising a dose release firing system configured to cause the adapter to move from its first position to its second position.

12. The inhaler of claim 11, wherein the refill assembly is releasable from the reusable assembly after it has been coupled to the reusable assembly.

13. The inhaler of claim 11, wherein the dose release firing system is breath-actuated.

14. The inhaler of claim 11, further comprising an axis that defines an axial direction that extends along or substantially parallel to the axis, wherein the refill assembly and the reusable assembly are configured to be coupled together by moving the refill assembly and the reusable assembly toward one another in the axial direction.

15. The inhaler of claim 11, wherein the dose release firing system includes a stored energy device configured to drive the adapter from its first position to its second position when stored energy in the stored energy device is released, wherein the dose release firing system is in a primed state when the stored energy is not released, and wherein the dose release firing system is in a fired state when the stored energy is released.

16. The inhaler of claim 11, wherein the reusable assembly further includes a flow governor for governing airflow through the inhaler.

17. The inhaler of claim 11, wherein the reusable assembly further includes at least one of a controller, a power source, a display, and a pressure sensor.

18. A refill assembly for use in a medicinal inhaler and configured to be removably coupled to a reusable assembly of the medicinal inhaler, the refill assembly comprising:
   a patient port;
   an adapter configured to cause a dose of medicament to be released, the adapter movable between a first position in which a dose of medicament is not released and a second position in which the dose of medicament is released; and
   a lockout member movable between (i) a first position in which the adapter is not movable from its first position to its second position, and (ii) a second position in which the adapter is movable from its first position to its second position; and
   an axis that defines an axial direction that extends along or substantially parallel to the axis, and wherein the adapter and the lockout member are movable in the axial direction relative to one another when the lockout member is in its second position;
   wherein the lockout member is in its first position when the refill assembly is not coupled to the reusable assembly and is in its second position when the refill assembly is coupled to the reusable assembly.

19. The refill assembly of claim 18, wherein when the lockout member is in its second position, the adapter is further movable from its second position to its first position.

20. The refill assembly of claim 18, wherein the reusable assembly includes a dose release firing system configured to cause the adapter to move from its first position to its second position.

* * * * *